(12) United States Patent
Truckai et al.

(10) Patent No.: US 7,220,951 B2
(45) Date of Patent: May 22, 2007

(54) SURGICAL SEALING SURFACES AND METHODS OF USE

(75) Inventors: Csaba Truckai, Saratoga, CA (US); John H. Shadduck, Tiburon, CA (US)

(73) Assignee: SurgRx, Inc., Redwood City, CA (US)

( * ) Notice: Subject to any disclaimer, the term of this patent is extended or adjusted under 35 U.S.C. 154(b) by 0 days.

(21) Appl. No.: 11/110,363

(22) Filed: Apr. 19, 2005

(65) Prior Publication Data

US 2005/0261678 A1    Nov. 24, 2005

Related U.S. Application Data

(60) Provisional application No. 60/563,424, filed on Apr. 19, 2004.

(51) Int. Cl.
*A05B 6/62* (2006.01)
*A61F 2/00* (2006.01)

(52) U.S. Cl. ........................................ 219/770; 607/96

(58) Field of Classification Search ................ 219/770, 219/764, 635, 771, 773; 607/1, 96, 114; H05B 6/62; A61F 7/00
See application file for complete search history.

(56) References Cited

U.S. PATENT DOCUMENTS

| | | | | |
|---|---|---|---|---|
| 659,409 A * | 10/1900 | Mosher | ........................ | 606/41 |
| 1,586,645 A * | 6/1926 | Bierman | ........................ | 606/51 |
| 1,798,902 A * | 3/1931 | Raney | ........................ | 606/45 |
| 1,881,250 A * | 10/1932 | Tomlinson | ........................ | 606/45 |
| 2,031,682 A * | 2/1936 | Wappler et al. | ........................ | 606/46 |
| 3,685,518 A * | 8/1972 | Beuerle et al. | ........................ | 606/51 |
| 3,730,188 A * | 5/1973 | Ellman | ........................ | 606/37 |

* cited by examiner

*Primary Examiner*—Daniel Robinson
(74) *Attorney, Agent, or Firm*—Townsend and Townsend and Crew LLP

(57) ABSTRACT

Various embodiments provide compositions that exhibit positive temperature coefficient of resistance (PTCR) properties for use in thermal interactions with tissue—including thermal sensing and $I^2R$ current-limiting interactions. Embodiments also provide tissue-engaging surfaces having PTCR materials that provide very fast switching times between low resistance and high, current-limiting resistance. One embodiment provides a matrix for an electrosurgical energy delivery surface comprising a PTCR material and a heat exchange material disposed within an interior of the matrix. The PTCR material has a substantially conductive state and a substantially non-conductive state. The heat exchange material has a structure configured to have an omni-directional thermal diffusivity for exchanging heat with the PTCR material to cause rapid switching of the PTCR material between the conductive state and non-conductive state. Preferably, the structure comprises a graphite foam having an open cell configuration. The matrix can be carried by tissue contacting surfaces of various electrosurgical devices.

16 Claims, 14 Drawing Sheets

SURGICAL SEALING SURFACES AND METHODS OF USE

CROSS-REFERENCES TO RELATED APPLICATIONS

This application claims the benefit under 35 USC 119(e) of U.S. Provisional Patent Application No. 60/563,424 filed Apr. 19, 2004, the full disclosure of which is incorporated herein by reference.

This application is also related to co-pending U.S. patent application Ser. No. 10/032,867, filed Oct. 22, 2001, titled Electrosurgical Jaws Structure for Controlled Energy Delivery; U.S. patent application Ser. No. 10/351,449, filed Jan. 22, 2003, titled Electrosurgical Instrument and Method of Use; U.S. patent application Ser. No. 10/443,974, filed May 22, 2003, titled Electrosurgical Working End with Replaceable Cartridges; U.S. patent application Ser. No. 10/993,210, filed Nov. 18, 2004, titled Polymer Compositions Exhibiting a PTC Property And Methods of Fabrication; Provisional U.S. patent application Ser. No. 60/523,567, filed Nov. 19, 2003, titled Electrosurgical Instrument and Method of Use; Provisional U.S. patent application Ser. No. 60/537,085, filed Jan. 16, 2004, titled Electrosurgical Working End with Replaceable Cartridge; Provisional U.S. patent application Ser. No. 60/552,978, filed Mar. 12, 2004 titled Electrosurgical Instrument and Method of Use; Provisional U.S. patent application Ser. No. 60/558,672, filed Apr. 1, 2004, titled Surgical Sealing Surfaces and Methods of Use; and U.S. patent application Ser. No. 10/781,925, filed Feb. 17, 2004, titled Electrosurgical Instrument and Method of Use, the full disclosure of all of which are incorporated herein by reference.

BACKGROUND OF THE INVENTION

1. Field of the Invention

Embodiments of invention relates to electrosurgical systems for sealing tissue. More particularly embodiment related to a probe or jaw structure that utilizes a polymeric positive temperature coefficient of resistance (PTC or PCTR) material in a sensing surface for control of thermal interactions with engaged tissue in (i) thermal sensing interactions and (ii) in $I^2R$ current-limiting interactions with tissue.

2. Description of Background Art

Positive temperature coefficient (PTC) device are known in electronic industries and are used as low power circuit protectors, thermal sensors and as constant temperature heaters. FIG. 1A is an exploded view of a current-limiting device or thermistor 5 that has a polymeric PTC material 10 sandwiched between a pair of foil electrodes (12a and 12b) and packaged within an insulator 14 (phantom view). FIG. 1B is a schematic view of a prior art current-limiting device or thermistor 5 in a circuit diagram showing that heating of the PTC material can limit current flow to the load 16. FIG. 1C is a schematic view of a PTC device 25 that consists of a constant temperature heating element for heating subject material 26 in contact with the device. In other words, the device of FIG. 1C comprises a PTC heater material that conducts heat to the engaged subject material 26. The use of a PTC material as a heating element as in FIG. 1C was proposed in a surgical jaw structure in U.S. Pat. No. 5,716,366 to Yates et al.

In previous PTC devices, the polymeric PTC material consists of a crystalline or semi-crystalline polymer (e.g., polyethylene) that carries a dispersed filler of conductive particles, such as carbon powder or nickel particles. In use, a polymeric PTC material will exhibit temperature-induced changes in the base polymer to alter electrical resistance of the polymer-particle composite. In a low temperature state, the crystalline structure of the base polymer causes dense packing of the conductive particles (i.e., carbon) into its crystalline boundaries so that the particles are in close proximity and allow current to flow through the PTC material via these carbon "chains". When the PTC material is at a low temperature, numerous carbon chains form the conductive paths through the material. When the PTC material is heated to a selected level, or an over-current causes $I^2R$ heating (Joule heating), the polymer base material thus will be elevated in temperature until it exceeds a phase transformation temperature. As the polymer passes through this phase transformation temperature, the crystalline structure changes to an amorphous state. The amorphous state causes the conductive particles to move apart from each other until the carbon chains are disrupted and no longer conduct current. Thus, the resistance of the PTC material increases sharply. The temperature at which the base polymer transitions to its amorphous state and affects conductivity is called its switching temperature $T_S$.

As long as the base polymer of the PTC material stays above its $T_S$, whether from external heating or from an overcurrent, the high resistance state will remain. Reversing the phase transformation allows the conductive particle chains to reform as the polymer recrystallizes to thereby restore multiple current paths (e.g., low resistance) through the PTC material.

Conductive polymer PTC compositions and their use as circuit protection devices are well known in the industry. For example, U.S. Pat. No. 4,237,441 (Van Konynenburg et al.), U.S. Pat. No. 4,304,987 (Van Konynenburg), U.S. Pat. No. 4,545,926 (Fouts, Jr. et al.), U.S. Pat. No. 4,849,133 (Yoshida et al.), U.S. Pat. No. 4,910,389 (Sherman et al.), U.S. Pat. No. 5,106,538 (Barma et al.), and U.S. Pat. No. 5,880,668 (Hall) and EP-730 282 A2 (Unitika) disclose PTC compositions that comprise thermoplastic crystalline polymers with carbon particles or other conductive particles dispersed therein. The disclosure of each one of these references is incorporated herein by this reference.

PTC devices are typically only employed in a passive role in an electronic circuit, and "switch" when a voltage spike overheats the polymeric material thereby causing its resistance also to spike. However, these devices do not consider the problem of rapid switching from a conductive to a resistive mode. There is a need for conductive polymer PTC compositions such as PTC composites which can switch in an extremely rapid, repetitive manner from a conductive to a resistive mode. There is also a need for PTC materials which have pixelated (localizable) switching across a surface of the PTC composition.

BRIEF SUMMARY OF THE INVENTION

Embodiments of the invention provide polymeric positive temperature coefficient (PTC) devices and methods of use that allows for spatially resolved thermal interactions with targeted tissue. Specific embodiments provide polymeric PTC based device that exhibit highly nonlinear PTC effects together with extremely rapid, repeatable switching at a selected switching temperature.

Many embodiment provide a polymeric PTC composition thermally coupled with a heat exchange means for rapid transfer of heat from a surface of the PTC material that engage thermally treated tissue. The inventive polymeric PTC device results in a highly stable current-limiting device that is capable of repeated cycling between an initial quiescent resistance and an operating resistance (or switching range).

One embodiment provides a matrix for an electrosurgical energy delivery surface comprising a positive temperature coefficient of resistance (PTC or PTCR) material and a heat exchange material dispersed within an interior of the matrix. The PTC material has a substantially conductive state and a substantially non-conductive state. The heat exchange material has a structure configured to have an omni-directional thermal diffusivity for exchanging heat with the PTC material to cause rapid switching of the PTC material between the conductive state and the non-conductive state. The matrix can be carried by tissue contacting surface of various electrosurgical devices such as the jaw surface of a forceps or a like device.

The structure of the heat exchange material can be cellular, open cell, crystalline or otherwise non-amorphous. Preferably, the structure comprises a graphite foam structure having an open cell or honey-comb like configuration. The foam structure can include a plurality of thermally conductive filaments, such as carbon fibers which can molded or otherwise incorporated into the matrix. The fibers can be oriented to conduct heat omni-directionally, bi-directionally or uni-directionally within the matrix and thus to and from portions of the PTC material. In particular, the conductive fibers can be configured to allow rapid conduction of heat from the surface of the matrix to adjacent or underlying PTC material to allow rapid switching of that material between conductive and non-conductive states during delivery of Rf energy. The conduction and switching can be done at micron scale to allow micron size portions of the matrix to be in a conductive states and adjacent portions to in a non-conductive state. This can be facilitated by increasing the concentration or number of conductive filaments near the surface portion of the matrix and/or configuring them to be have a selected conduction direction. The matrix can also include a doped conductive layer, which can be electrically insulated from the heat exchange material.

The heat exchange material can be configured to perform several different thermal functions. For example, it can be configured to not only conduct heat but also to act as a heat sink by coupling with a passive heat sink, a phase change material or other heat storage means known in the art. The phase change material can be a polymeric material which can infill the cellular or other portions of the foam structure. The matrix can also be configured to function as a heat sink through the use of active heat sinks such as thermal siphons or cooling channels or a combination of both.

In an exemplary embodiment of a method of using the matrix for delivering energy to tissue, tissue is engaged with an electrosurgical energy delivery surface including a matrix comprising a positive temperature coefficient of resistance (PTC) material and a heat exchange material disposed within an interior of the matrix. The energy deliver surface is then used to deliver Rf energy to tissue to ohmically heat tissue in a target tissue volume. The delivery of Rf energy to the tissue is modulated utilizing the heat exchange material to exchange heat with the PTC material to cause rapid switching of the PTC material between substantially conductive and substantially non-conductive states. This results in the production of a substantially uniform thermal effect in the target tissue volume as well as the prevention of electrical arcs in tissue and/or tissue charring due to one or more of arcing, tissue desiccation or overheating of tissue. Such thermal effects can include collagen and other protein denaturation and the generation of tissue welds and seals including high strength welds formed in part formed by the fusion of the denatured collagen.

The switching process can be configured to not only produce a uniform thermal effect in tissue but also serve to substantially prevent or reduce charring and/or electrical arcing into tissue. This is achieved because before the tissue is heated to level at which charring and arcing can occur, the matrix is able to locally sense the temperature/resistance of a given tissue portion via thermal conduction through the matrix and then rapidly switch to a non-conductive state to cease the delivery of Rf energy and thus ohmic heating of that portion. When the tissue cools down, the matrix is then able to rapidly switch back to a conductive mode. This process allows for the production of tissue welds and seals in a target tissue volume containing a number of different types of tissue, for example, fascia, muscle, and other soft tissue because the matrix is able to spatially sense the temperature/resistance of each tissue type in contact with the delivery surface and then spatially modulate the delivery of energy accordingly. In particular, it allows for the generation of high strength fluidic seals in blood vessels including arteries by spatially modulating the delivery of energy to denature and then fuse the collagen in the vessel wall.

Particular embodiments provide a polymeric PTC-based electrosurgical device configured to disallows $I^2R$ heating at electrosurgical energy parameters. In other words, such PTC material cannot heat itself at electrosurgical energy delivery parameters. Related embodiments provide a polymeric PTC material that can switch extremely rapidly between a low base resistance value and a very high resistance value, for example, many times per second. Such embodiments can include a PTC-based thermistor for use in very rapid repetitive use (i.e., switching) such as is necessary in telecommunications devices and equipment. Still other related embodiments provide a polymeric PTC based electrosurgical systems that can spatially modulate current flow across a tissue contacting of an electrosurgical devices such a forceps. Such system can utilize polymeric PTC materials configured to allow for high spatial resolution, herein called pixelated resolution, for highly localized switching across a surface of the PTC material that engages tissue.

BRIEF DESCRIPTION OF THE DRAWINGS

The accompanying drawings are included to provide a further understanding of embodiments of the invention and are incorporated in and constitute a part of this disclosure. The embodiments in the drawings taken together with the description serve to explain the principles of the present invention.

DETAILED DESCRIPTION OF THE INVENTION

Figure 1A:
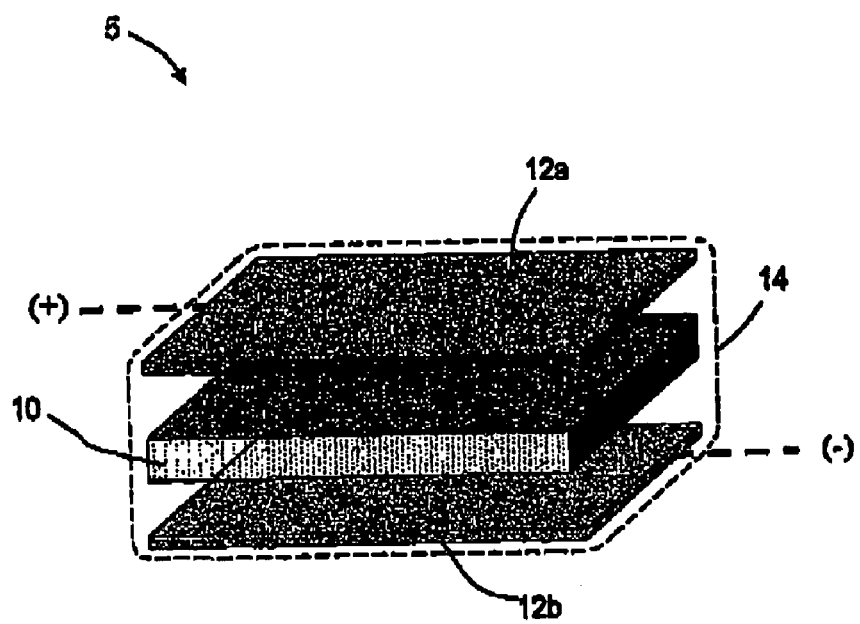
FIG. 1A is an exploded schematic view of a prior art current-limiting device with a polymeric PTC body sandwiched between first and second electrodes.

Operational principles of polymeric PTC devices for sensing surfaces. Various embodiments of the invention provide polymeric compositions that exhibit positive temperature coefficient of resistance (PTC or PTCR) effects. Embodiments also provide devices and systems which utilize those PTC compositions in various applications including for example, electrosurgical, telecommunication, sensing and related applications. Particular embodiments provide PTC-based electrosurgical instruments systems and devices configured to provide: (i) high spatial resolution in thermal sensing functionality and (ii) contemporaneous pix-elated current-limiting functionality. Embodiments of such PTC based systems herein are referred to at times as "dual function" PTC systems and/or devices.

Describing a material as having a positive temperature coefficient (PTC) of resistance simply means that the resistance of the material increases as temperature increases. Many metal-like materials exhibit electrical conduction that has a slight positive temperature coefficient of resistance. (Materials that conduct like metals have the lowest resistivity of all non-superconducting materials, wherein resistivity generally falls in the range of 1-100 μΩ-cm.). In such metal-like materials, the PTC's variable resistance effect is characterized by a gradual increase in resistance that is linearly proportional to temperature—that is, a linear PTC effect.

A "nonlinear" PTC effect is exhibited by certain types of polymer matrices that are doped with conductive particles. These polymer PTC compositions have a base polymer that undergoes a phase change or glass transition temperature $T_G$, wherein the PTC composition has a resistance that increases sharply or otherwise non-linearly over a narrow temperature range (see FIG. 2). Many embodiments of the invention relate to the use of such non-linear PTC materials.

For ease of discussion, an explanation will now be provided of various terms relating to operational characteristics of polymeric PTC compositions. These terms have the meaning given unless otherwise indicated in the specification:

$T_S$: Switching temperature: this is temperature at which the composition exhibits a very large nonlinear PTC effect; that is it will "trip" to very high current-limiting resistivity from low quiescent resistivity;

$T_G$: Glass transition temperature: this is the temperature at which polymeric base material transitions from a glass state to a rubbery state;

$T_M$: Melt temperature: this is the temperature at which a crystalline material transitions from a nonflowable state to flowable state;

$I_{Hold}$: Hold current: this is maximum current a PTC composition will sustain for a selected time interval at a certain temperature (e.g., 20° C.);

$I_{Trip}$: Trip current: this is the minimum current that will cause a PTC composition to reach its switching range to become non-conductive at a certain temperature (e.g., 20° C.);

$V_{Max}$: Maximum voltage: this is maximum voltage a PTC composition withstands without damage;

$I_{Max}$: Maximum current: this is the maximum current a PTC composition withstands without damage;

$R_{IL}$: This is the minimum resistance of a PTC composition in an initial quiescent state;

$R_{AT}$: This is the maximum resistance of a PTC composition in non-tripped state after cycling between quiescent and operational states; and $P_D$Max: This the power dissipated from a PTC composition when tripped at its switching range.

When describing properties of the base polymer used in a PTC composition, it is useful to further explain the terms glass transition temperature ($T_G$) and melting temperature ($T_M$). Glass transition temperature is not the same as melting temperature. A transition at $T_M$ occurs in crystalline polymers when the polymer chains fall out of their crystalline phase, and become a disordered deformable or flowable media. A glass transition at $T_G$ is a transition which occurs in amorphous polymers (i.e., polymers whose chains are not arranged in ordered crystals) where the polymer transitions from glassy state in which it is relatively hard and rigid to a rubbery state. A glass transition temperature ($T_G$) in a crystalline polymer is herein loosely defined as a temperature point where the polymer experiences a significant change in its mechanical and/or rheological properties—such as a large change in its Young's modulus (also known as modulus of elasticity). The $T_G$ is the temperature at which the polymer structure turns "rubbery" upon heating and "glassy" upon cooling. Crystalline polymers also go through a stage of becoming leathery before becoming rubbery. There is a loss of stiffness (modulus of elasticity) in both of these stages. Such crystalline polymers or domains have a sharp, defined melting point $T_M$. In contrast, while an amorphous polymer is in a solid or rigid state below $T_G$ and rubber above that temperature, its transition from being rigid to flowable occurs over a wide temperature range as opposed to distinct temperature such melting point temperature for crystalline material.

A discussion will now be presented of the thermodynamic equations and relations useful in understanding the operating characteristics of PTC materials. The temperature-induced variable resistance of a polymer PTC composition when used in a prior art current-limiting application is based on an overall energy balance—and can be described by Equation (1) below. It is useful to describe the basic thermal/resistance properties of a polymeric PTC composition, to thereafter explain how non-linear PTC effects and rapid switching are achieved in a "system" corresponding to the invention.

$$mC_p(\Delta T/\Delta t) = I^2 R - U(T - T_a) \qquad (1)$$

Wherein:

m=mass of the PTC composition $C_p$=specific heat capacity of the PTC composition (at a constant pressure)
$\Delta T$=change in temperature of the PTC composition
$\Delta t$=change in time
I=current flowing through the PTC composition
R=resistance of the PTC composition
U=overall heat-transfer coefficient
T=temperature of the PTC composition
$T_a$=ambient temperature In equation (1) above, the current flowing through the PTC composition generates heat at a rate equal to $I^2R$. All or some of the heat can be subtracted by interaction with the environment at a rate described by the term $U(T-T_a)$. Any heat not subtracted by environmental interaction raises the temperature of the PTC composition at a rate described by the term:

$$mC_p(\Delta T/\Delta t) \qquad (2)$$

To keep Equation (1) as simple as possible, assume a uniform temperature across the polymeric PTC composition.

If the heat generated by the polymeric PTC composition and the heat subtracted to the operating environment are in balance, T/t goes to zero, and Equation (1) can be rewritten as:

$$I^2R = U(T-T_a) \qquad (3)$$

Figure 2:
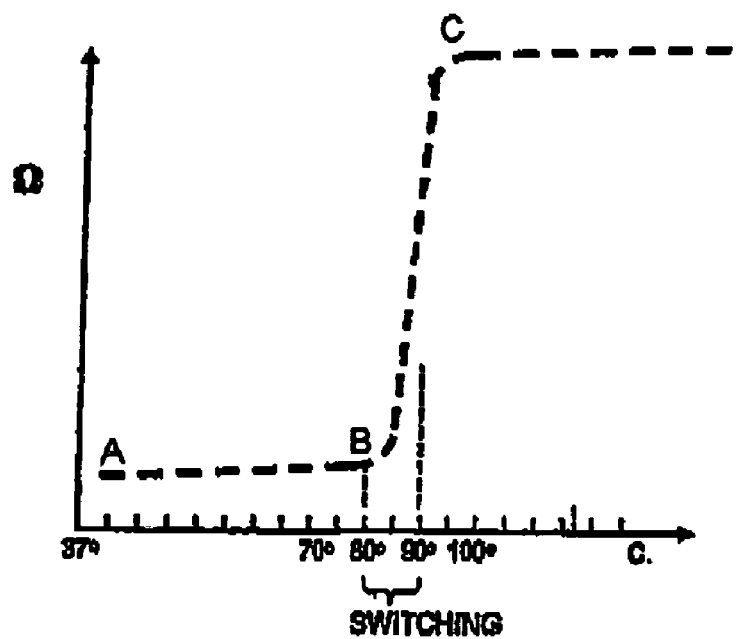
FIG. 2 is an exemplary temperature-resistance curve of a polymeric PTC composition.

Under certain operating conditions, the heat generated by the PTC composition and the heat lost by the device to the environment can be in balance at a relatively low temperature—for example, Point A in FIG. 2. If the current flow (I) through the PTC composition increases and the ambient temperature remains constant, the heat generated by the PTC composition increases, and the temperature of the PTC composition also increases. But if the increase in current is not too large, all the generated heat can be lost to the environment, and the PTC composition will stabilize according to Equation (3) at a higher temperature, such as Point B in FIG. 2.

If the ambient temperature (or tissue engaged by the PTC composition) increases instead of the current, the PTC composition will stabilize according to Equation (3) at a higher temperature (possibly again at Point B in FIG. 2). Point B in FIG. 2 can also be reached as a result of an increase in current (I) and an increase in ambient temperature. Further increases in either or both of these conditions will cause the PTC composition to reach a temperature $T_S$ at which the resistance rapidly increases (e.g., Point C in FIG. 2).

Any further increase in current or ambient temperature will cause the PTC composition to generate heat at a rate greater than the rate at which heat can be lost to the environment, causing the PTC composition to heat up rapidly. At this stage, large increases in resistance occur with small changes in temperature. In FIG. 2, this occurs between Points B and C, and this vertical or "square" portion of the curve defines the operating region of the PTC composition in its tripped state. The large change in resistance causes a corresponding decrease in current flow in the circuit.

Because the temperature change between Points B and C in FIG. 2 is very small, the term $(T-T_a)$ in Equation (3) can be replaced by the constant $(T_S-T_a)$, where $T_S$ is the operating (current-limiting) temperature of the device. Then Equation (1) can be rewritten as:

$$I^2R = V^2/R = U(T_S-T_a) \qquad (4)$$

Because U and $(T_S-T_a)$ are now both constants, Equation (4) reduces to $I^2R$=constant; that is, the device now operates in a constant power state. Expressing this constant power as $V^2/R$ emphasizes that, in the tripped state, the PTC composition resistance is proportional to the square of the applied voltage. This relation holds until the device resistance reaches the upper "square" region of the curve (Point C in FIG. 2).

For a PTC composition that has tripped, as long as the applied voltage is high enough for the resulting $V^2/R$ to supply the $U(T_S-T_a)$ loss, the PTC composition will remain in the tripped state; that is, the PTC composition will remain non-conductive. When the voltage is decreased to the point at which the $U(T_S-T_a)$ loss can no longer be supplied, the PTC composition will "reset" or return to its quiescent base resistance.

Figure 1B:
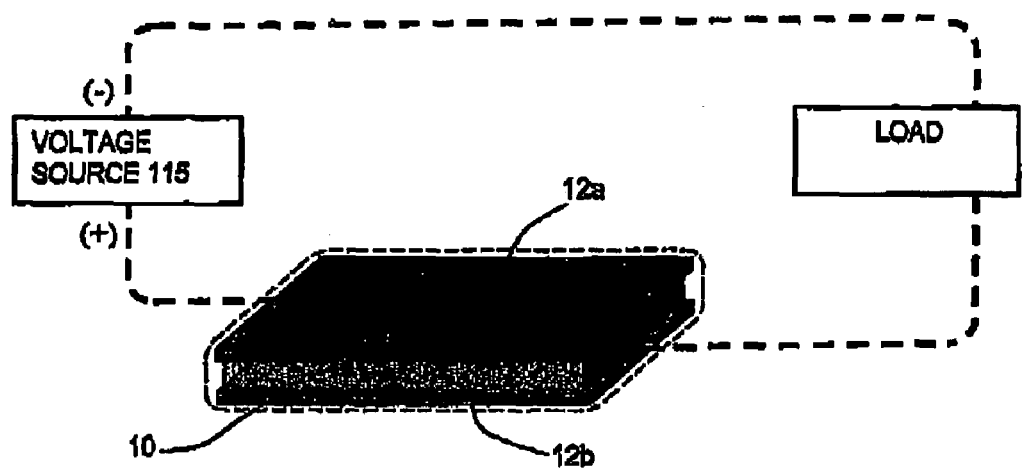
FIG. 1B is a schematic view of a prior art current-limiting device or thermistor in a circuit diagram.
Figure 1C:
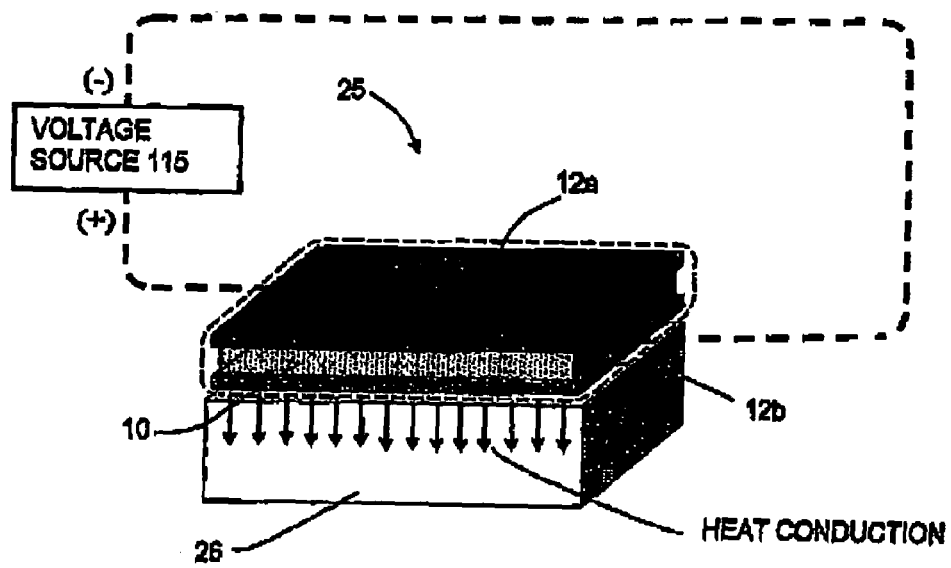
FIG. 1C is a schematic view of a prior art constant temperature heating device in a circuit diagram.

In the context of FIGS. 1B and 1C, it can be understood how the above equations describe the operation of a PTC composition in a current-limiting device (cf. FIG. 1B) and a constant temperature heating device (cf. FIG. 1C).

Various embodiments of the invention provide systems and devices that allows for a very rapid bi-directional switching ($\Delta t$) along the resistance-temperature curve of FIG. 2 (indicated by arrow 100). Many embodiments provide polymeric PTC compositions that exhibits a resistance-temperature curve with a high degree of "squareness" at its $T_S$ (at Point C in FIG. 2). Specific embodiments provide a "system" that combines a passive heat exchange component within the polymeric PTC composition to optimize heat subtraction from matrix 50, which relates to "U"—the overall heat-transfer coefficient in the equation:

$$mC_p(\Delta T/\Delta t) = I^2R - U(T-T_a) \qquad (5)$$

In other words, referring to the exemplary jaw structures of FIGS. 3-6, the heating of the PTC matrix 50 can be entirely limited to external heating of the matrix surface by engaged tissue T when the jaw includes a heat exchange component 60 which can comprise a heat exchange material 60. In various embodiments, heat exchange component 60 can comprise any passive or active means for one or more of the rapid subtraction, diffusion, or transfer of heat from an electrosurgical tissue-engaging surface that utilizes a PTC material to sense tissue temperature while modulating ohmic heating in the engaged tissue. Further, heat exchange component 60 can comprise a number of heat exchange materials known in the art including, without limitation, heat subtraction materials which can in turn include without limitation metals, graphite structures, heat pipes or thermosiphons, phase change materials, nano-materials, refractory materials, liquids and the like. For ease of discussion heat exchange component 60 will now be described as a heat subtraction component 60, but other embodiments are equally applicable In various embodiments, heat subtraction component 60 is configured to very rapidly diffuse away or otherwise transfer or dissipate heat conducted to the tissue-engaging surface that comprises a PTC sensing device or otherwise includes PTC materials.

Figure 3:
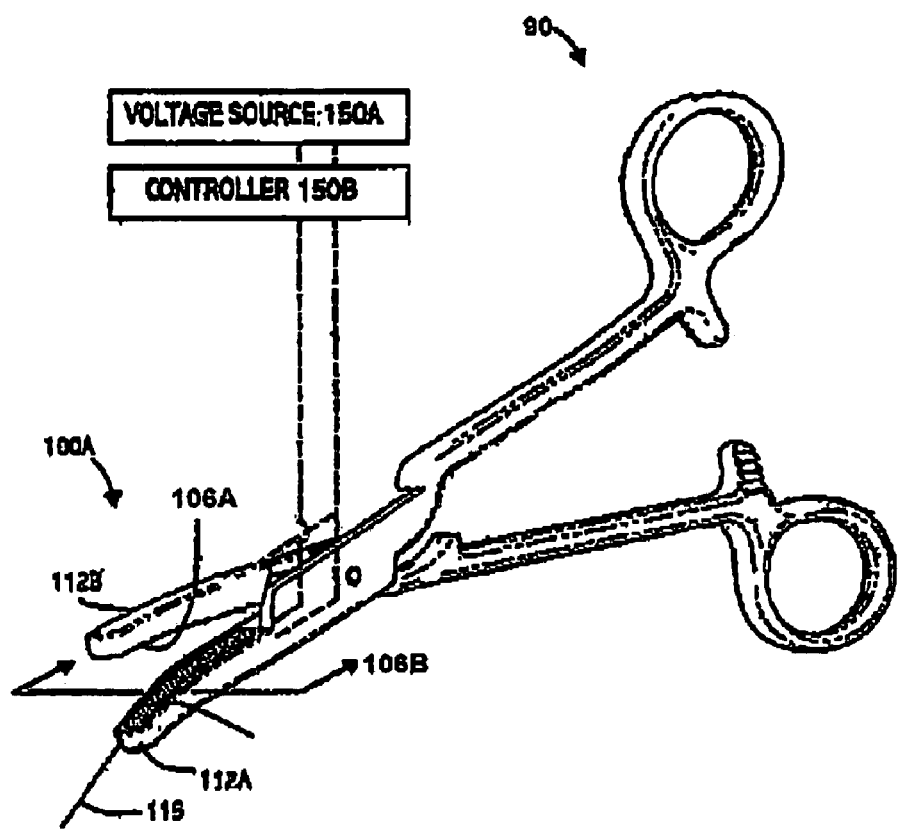
FIG. 3 is a perspective view of a surgical forceps with an electrosurgical jaw structure that carries the PTC sensing surface of the invention.
Figure 4:
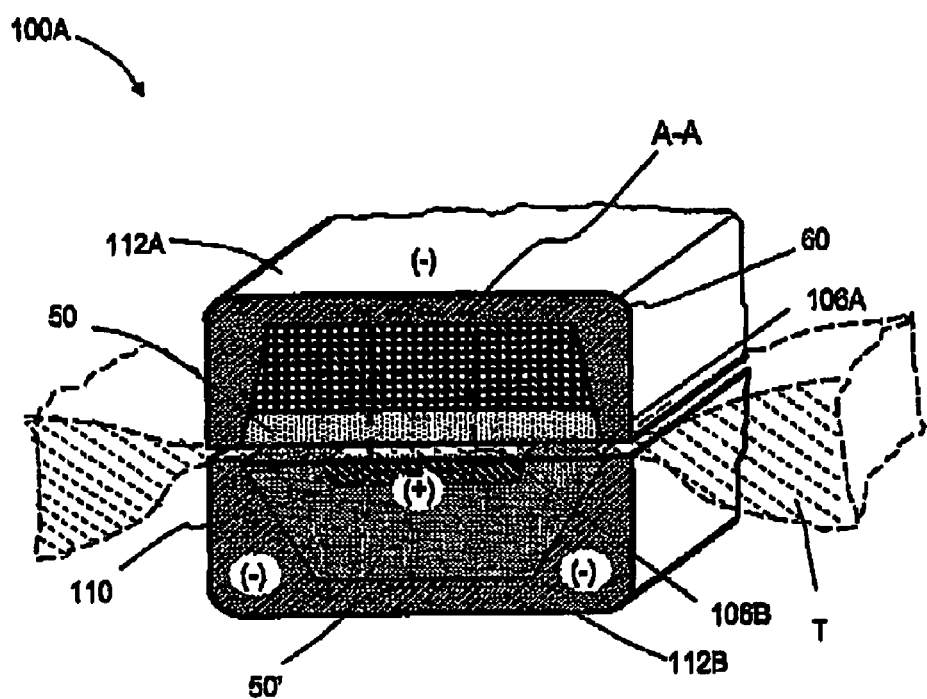
FIG. 4 is an enlarged view of the PTC sensing surface of the jaws as in FIG. 3 taken along line AA of FIG. 3.

A discussion will now be presented of the uses of various embodiments of PTC compositions in electrosurgical devices and related surgical applications. FIG. 3 illustrates an exemplary embodiment of a forceps-type electrosurgical instrument 90 that can use a PTRC based matrix 50 to modulate or the control delivery of radio-frequency (Rf) energy to tissue for one or more electrosurgical procedures such as tissue welding. It should be appreciated that forceps 90 is but exemplary instrument and other electrosurgical instruments and devices known in the art such as a scissors, scalpels, resection tools, tissue ablation instruments and the like. Forceps 90 includes a working end or electrosurgical jaw structure 100A has tissue-engaging surfaces 106A and 106B in first jaw element 112A and second jaw element 112B that close or approximate about axis 115 that is straight or curved. It should be appreciated that in various embodiments, the jaw elements can be of any curved or straight shape (or a combination of both) configured for open or endoscopic surgeries with scissors-type actions or with one or more cam mechanism as is known in the art. The jaws also can carry a sliding cutting blade as described in U.S. patent application Ser. No. 10/443,974, filed May 22, 2003 titled Electrosurgical Working End with Replaceable Cartridges, and Provisional U.S. Patent Application Ser. No. 60/537,085 filed Jan. 16, 2004 titled Electrosurgical Working End with Replaceable Cartridge. FIG. 4 graphically illustrates the opposing jaws 112A and 112B engaging tissue T, with an electrode 110 having an exposed surface.

Figure 5:
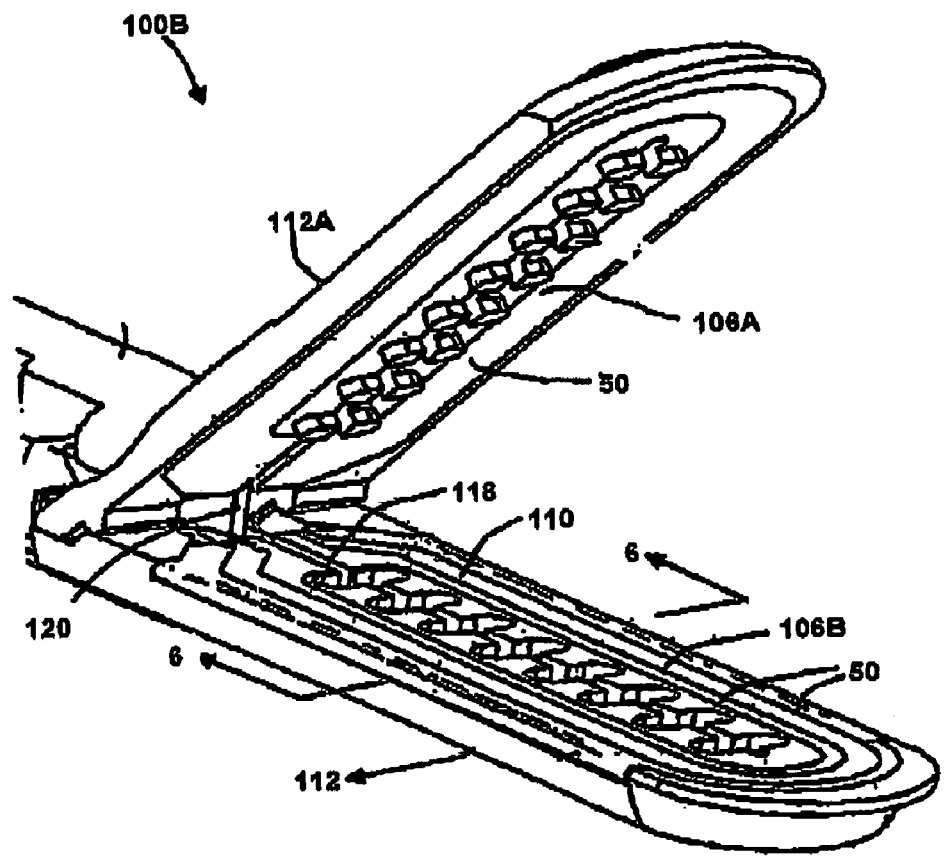
FIG. 5 is a perspective view of an alternative high-compression electrosurgical jaw structure that carries the PTC sensing surface of the invention.
Figure 6:
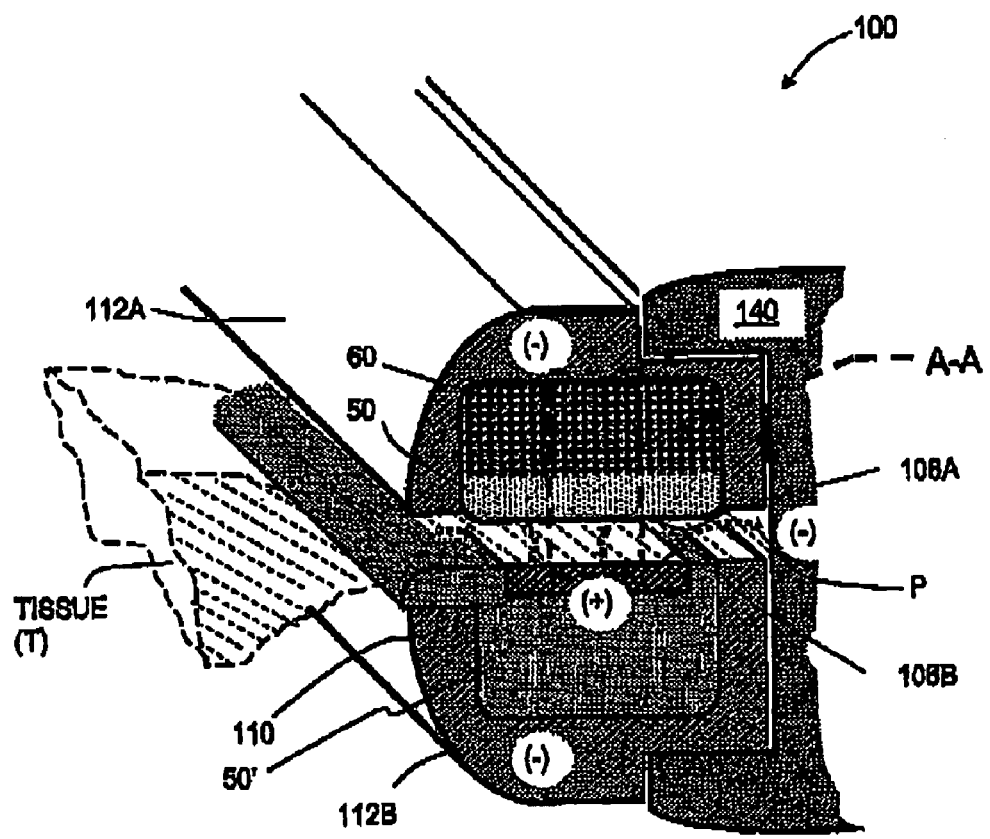
FIG. 6 is an enlarged view of the PTC sensing surface of the jaws of FIG. 4 taken along line AA of FIG. 5.

FIGS. 5 and 6 depict an alternative embodiment of a working end with jaw structure 100B that can carry the same PTC matrix 50 and heat subtraction component 60 as the forceps-type jaw structure of FIGS. 3 and 4. The jaw structure 100B of FIG. 5 carries a blade for transecting the welded tissue. FIG. 6 illustrates a cross section of the upper and lower jaws 112A and 112B of FIG. 5 with a central blade slot 118 for receiving the slidable blade member 120. On either side of the blade slot 118, the jaw bodies carry variable resistive matrices 50 (and 50') that are similar (or identical) to the matrices depicted in FIGS. 3 and 4. In the exemplary embodiment of FIG. 5, the lower jaw 112B has a matrix 50' with electrode 110 being exposed in the center of the jaw's engagement surface 106B with a portion of the PTC matrix 50' extending laterally on either side of blade slot 118 as well as within the interior of the jaw. As can be seen in FIG. 5, matrix extends in a "U"-shape around the end of blade slot 118 to allow welding of engaged tissue around the end of a welded and transected tissue region.

In many embodiments, the working ends 100A and 100B of FIGS. 3-6 are configured to function to modulate Rf energy application to tissue in multiple potential current paths as depicted, for example, in FIG. 6. FIG. 6 illustrates the working end 100B engaging tissue with a graphical depiction of the potential Rf current paths P in tissue and across regions of the PTC matrices.

Figure 7:
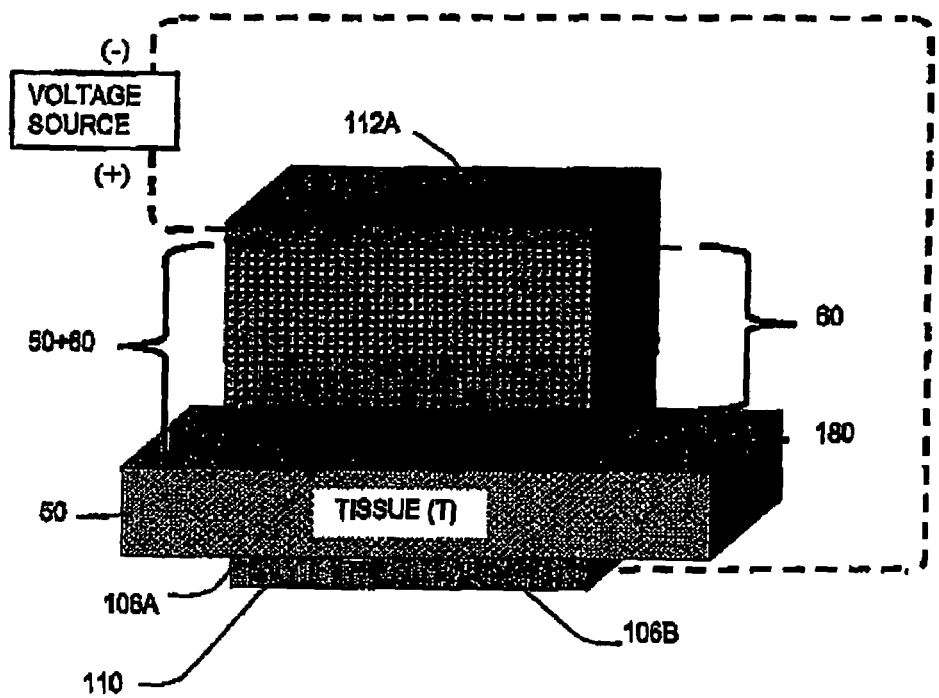
FIG. 7 is a schematic view of the PTC sensing surface with passive cooling component taken along line A-A of the electrosurgical jaw structure of either FIG. 4 or FIG. 6.

In one preferred embodiment, illustrated in FIGS. 3-6 and schematically in FIG. 7, a system of the invention combines a polymeric PTC matrix 50 with a heat subtraction material 60 having a high thermal diffusivity property. It is believed that certain graphite foams offer the highest thermal diffusivity of any known material, and is suited for heat subtraction from engagement surface 106A. The term "thermal diffusivity" defines a measure of how quickly heat is transported through the material compared with how quickly the material absorbs the heat. Thermal diffusivity thus is defined as thermal conductivity divided by the product of density and specific heat. Suitable graphite foams include POCO-FOAM commercially available from Poco Graphite, Inc., 300 Old Greenwood Rd., Decatur, Tex. 76234. This material has a very high thermal conductivity, coupled with low density and low specific heat, resulting in high thermal diffusivity.

Carbon foam materials are composed of amorphous carbon and have densities ranging from 0.12 to 0.50 g/cm$^3$. Generally, carbon amorphous structures have good thermal insulating properties with thermal conductivities less than 10 W/m K. However, PocoFoam™ is derived from mesophase pitch, an intermediate phase in the formation of carbon from pitch that when heated above 2000° C. forms graphite. This precursor material, combined with an innovative production method, produces a material with very high thermal conductivity. It differs from conventional carbon foams in that the ligaments making up the honeycomb-like structure of the foam are of a highly aligned and crystalline-like structure rather than being strictly amorphous as in other carbon foams. The difference in such molecular alignments gives this carbon foam its very high thermal conductivity. Another advantage of this foam, compared with other materials that also have high thermal conductivities such as carbon-carbon composites and graphite fibers, is that this preferred foam conducts heat in all directions. Composites and fibers only conduct well in the direction of the fiber.

2. Method of interaction enabled by PTC devices with sensing surfaces. The need for a polymeric composition that exhibits a highly nonlinear PTC effect and well as a repeatable, very fast switching time arose from new inventions in the field of electrosurgery (see, e.g., the authors' co-pending U.S. patent application Ser. No. 10/032,867). In delivering energy to biological tissue to perform tissue-welding procedures, it was determined that a variable resistive material was needed that could accomplish new types of thermal and electrical interactions with tissue, viz., the combination of a temperature sensing function and a current-limiting function for modulated I$^2$R (ohmic) tissue heating. Further, it was determined that the variable resistive PTC composition would need to be highly sensitive in functioning in a thermal sensing role—to thereby provide very high spatial resolution to the thermal sensing function and to provide contemporaneous application of electrical energy with the same very high spatial resolution. By the term spatial resolution, it is meant that the variable resistive PTC material provides, effectively, a "pixelated" operating surface wherein some pixels (or spatial regions) of the PTC surface are above its switching temperature, $T_S$, while adjacent pixels or regions are below its $T_S$. This material property is achieved by the development of a polymer body (or surface layer) exhibiting a highly nonlinear PTC effect and a very rapid and localizable switching speed, as described above. In one embodiment, the switching speed at a local region of the engagement surface of the PTC device is greater than 10 Hz. More preferably, the switching speed in greater than 20 Hz, and still more preferably is greater than 30 Hz. In one embodiment, the PTC matrix is configured to be incapable of I$^2$R heating when engaging tissue and has an internal resistance of an order of magnitude less than the resistance of engaged tissue. More preferably, the PTC matrix has an internal resistance of two orders of magnitude less than the resistance of engaged tissue; and still more preferably the PTC matrix has an internal resistance of three orders of magnitude less than the resistance of engaged tissue.

Various embodiments of the invention are well suited to electrosurgical applications in part, based on two considerations. First is the fact that the target biological tissue exhibits properties that are non-uniform and dynamic during the process of I$^2$R (ohmic) heating. Therefore, embodiments of an electrosurgical instrument having a PTC matrix are desirably able to thermally sense temperature non-uniformity across the spatial geometry of a tissue-engaging surface 106A of the PTC body—in effect a pixelated sensing function. Second, the PTC matrix desirably exhibits corresponding non-uniform heating across the pixelated PTC surface correspond able to the sensed tissue temperatures, resulting in dynamic, non-uniform, pixelated resistivity. In use these properties can be applied to allow the PTC surface to apply pixelated I$^2$R or ohmic heating within the engaged tissue regions to heat them to a targeted temperature to achieve a desires tissue effect such as uniform protein denaturation, tissue welding, high strength tissue welding, etc. Further, the PTC matrix can adjust in resistivity very rapidly to prevent arcing and tissue charring at the interface of the tissue and the electrosurgical surface.

Figure 8:
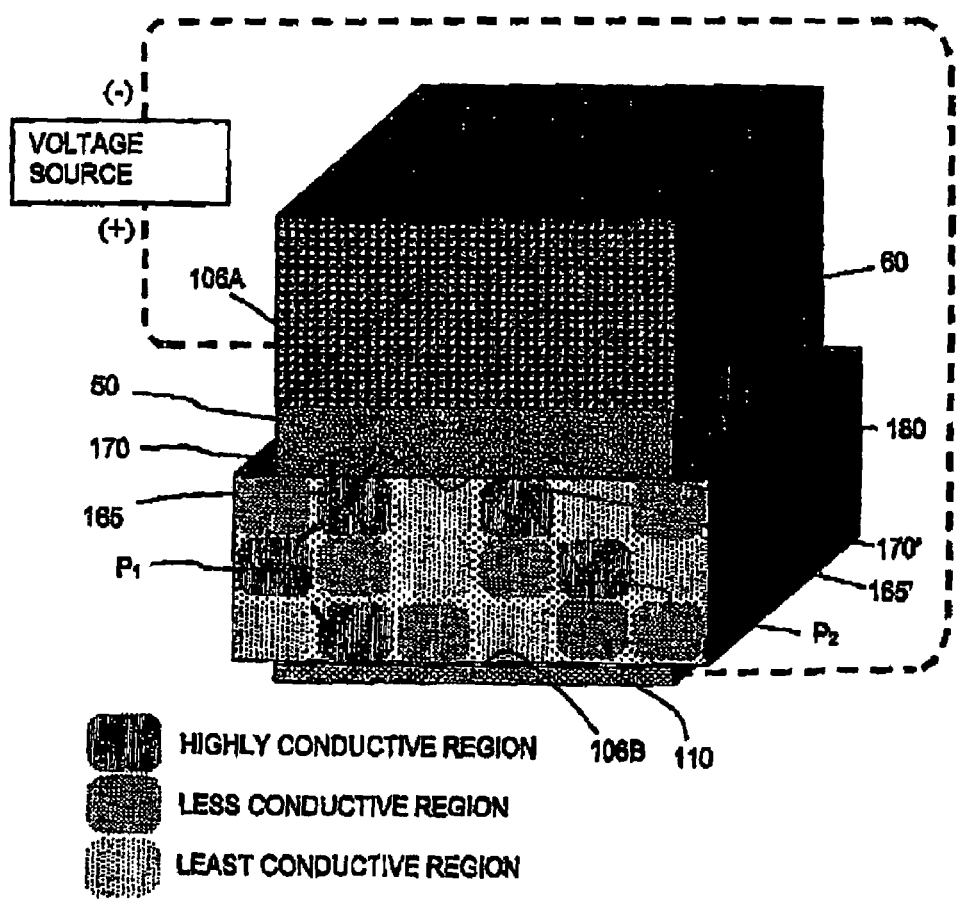
FIG. 8 is a schematic view of the PTC sensing surface of FIG. 7 further depicting a method of the invention in interacting with tissue.

FIGS. 7 and 8 schematically depict a portion of a jaw structure (as in FIGS. 3-6) wherein the arrangement of the polymeric PTC composition 50 in relation to the subject material (biological tissue T or otherwise) differs from conventional uses of PTC materials as depicted in FIGS. 1B and 1C. In FIGS. 6 and 7 it can be seen that the PTC composition 50 can be adapted to directly engage and interact with surface 106A of the subject material T, without any interposed electrically insulative coating (cf. FIGS. 1B and 1C). In use, such embodiments allow for the surface 106A or the jaw surface of another electrosurgical device to contemporaneously interact with the subject material 110, in both heat sensing and $I^2R$ heating modes of operation.

Accordingly, various embodiments of the invention provide electrosurgical methods for treating tissue wherein a surface of an electrosurgical devices having a PTC composition 50 described herein contemporaneously interacts with the subject material 110, using both heat sensing and $I^2R$ heating functionality. One such embodiment shown in FIG. 7. comprises (i) providing a polymeric PTC composition that substantially disallows $I^2R$ heating and thus prevents a nonlinear PTC effect therein; (ii) engaging the PTC composition with the subject material or tissue T; (iii) coupling a voltage source 150A to the PTC composition and the subject material in a series circuit to cause current flow resulting in an $I^2R$ heating interaction within the subject material; (iv) allowing heat within the subject material or tissue T to transfer to and interact with PTC composition 50 to cause a nonlinear PTC effect therein to modulate $I^2R$ heating in the subject material, and (iv) allowing the heat subtraction component 60 to rapidly diffuse heat away from the PTC material's surface 106A.

Various embodiments of the invention utilizing PTC materials can be configured to have a functionality useful for producing selected thermal effects in material including uniform heating of materials. Specific embodiments can be configured to provide uniform heating of materials that have non-uniform or dynamic electrical properties, such as biological tissue, as depicted in more detail in FIG. 8. In this embodiment, heat subtraction component 60 comprises a graphite foam 60 described herein but other heat subtraction components are equally applicable. In FIG. 8, the tissue's electrical non-uniformity is indicated graphically by three hatching shades. In such electrosurgical interaction with tissue, an alternating current is used. It can be understood that voltage source 150A will apply current through the series circuit and in a microcurrent path $P_1$ in tissue that defines the least resistance through the tissue. The alternating current along path $P_1$ in the tissue will cause $I^2R$ heating therein. The localized ohmically ($I^2R$) heated tissue indicated at 165 that engages region 170 of PTC composition 50 will then be passively heated by conduction from the tissue. In turn, that region 170 of the PTC composition functions as a sensor and responds at about its $T_S$ to contemporaneously become highly resistive. At the same time adjacent tissue 165' that is most conductive engages PTC region 170' that is also in its low resistance state. The highly localized heating of PTC "pixel" indicated at 165 then will cause microcurrent paths to shift to the more conductive path, $P_2$. As any surface pixel of the PTC material is elevated in temperature, graphite foam 60 very rapidly diffuses the heat thus causing the pixel to switch back to its conductive state—unless still heated by ohmic effects in the adjacent tissue.

Embodiments of the system allows for highly dynamic, spatial resolution of pixelated resistivity and current flow across the surface of the PTC composition 50. Further, the graphite foam, operating as a heat subtraction component, will rapidly diffuse heat to thus make the PTC device switch faster.

Still referring to FIG. 8, in particular embodiments for fabrication of PTC materials, the polymeric PTC material 50 is melted so as to flow into the open cells of the graphite foam 60. This results in a coupling between the high surface area of the foam and the polymer that is extremely well suited for thermal conduction. In this embodiment, a substantially thick layer of PTC indicated at 180 is provided at the sensing or engagement surface 106A, since the graphite is electrically conductive and needs to be maintained inward of the surface. In another more preferred embodiment, the graphite foam is coated with a coating that is substantially thermally conductive but electrically non-conductive. A thin polymer can serve this purpose. In this embodiment, the layer of PTC material 180 would remain at the sensing or engagement surface, but the graphite foam could extend closer to the tissue-engaging surface.

Figure 9:
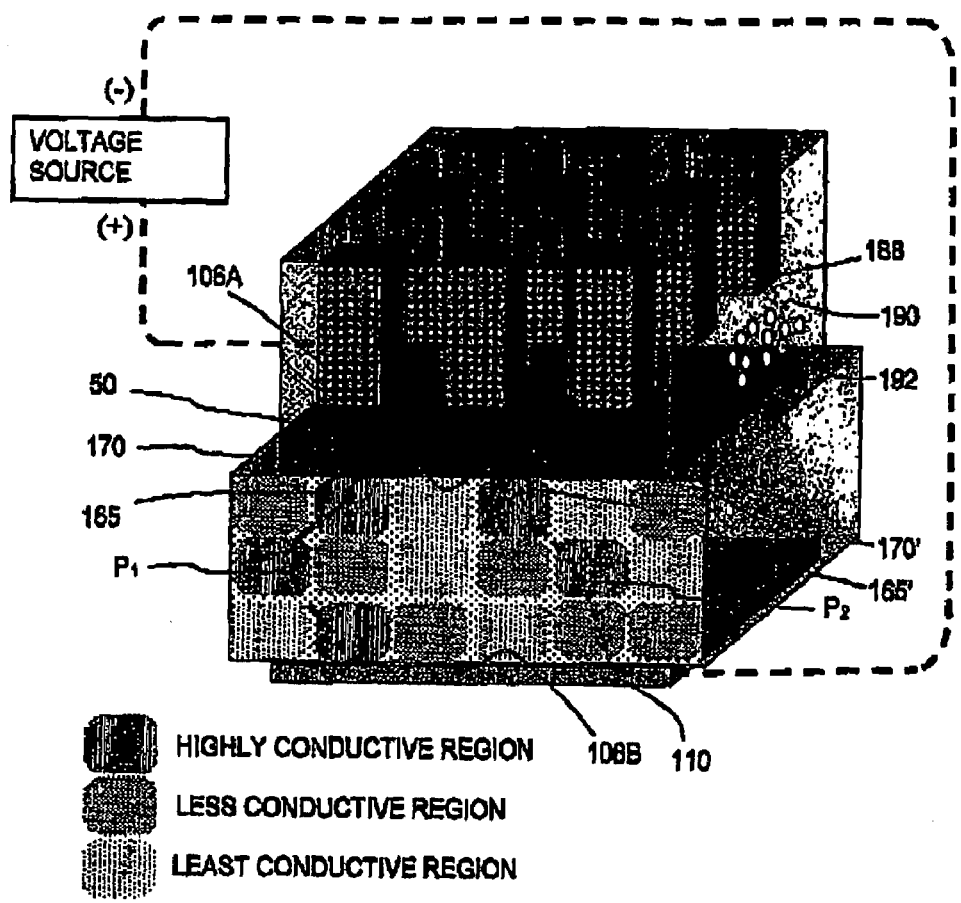
FIG. 9 is a schematic view of an alternative PTC sensing surface with spaced apart heat diffusing elements.

In another more preferred embodiment of PTC system 185 illustrated in FIG. 9, the graphite foam 60 can be formed in pixels or posts 188 that are spaced apart in the polymeric PTC material 50. In this embodiment, it can easily be understood that the heat diffusion will be induced to be in the direction of arrows generally orthogonal to the plane of the PTC sensor surface 106A. This embodiment will thus prevent the lateral diffusion of heat which in turn will enhance spatial resolution of the PTC material's switching capabilities.

3. Methods of fabrication of polymeric PTC devices for sensing surfaces. A discussion will now be presented of methods of fabrication of various embodiments PTC materials. These methods are exemplary and other methods known in the art may be used. Various embodiments of the polymeric PTC compositions described herein comprise a matrix of a base polymer 190 with electrically conductive particles 192 dispersed therein as is known in the art. The base polymer component 190 can be a crystalline or semi-crystalline polymer such as in the polyolefin family and more particularly a polyethylene. Suitable polyethylenes include without limitation HDPE, LDPE, MDPE, LLDPE. The base polymer component 190 also can be a copolymer of at least one olefin and one or more other monomers known in the art that can be co-polymerized with the olefin. Other suitable base polymer component include without limitation polyamide, polystyrene, polyacrylonitrile, polyethylene oxide, polyacetal, thermoplastic modified celluloses, polysulfones, thermoplastic polyesters (e.g., PET), poly (ethyl acrylate), or poly(methyl metbacrylate). Other suitabel co-polymers include without limitation, NYLON, fluoropolymers such as polyvinylidene fluoride and ethylene tetrafluoroethylene, or blends of two or more such polymers. In preferred embodiments, the polymer base component 190 can be any high-density polyethylene, low-density or medium-density polyethylene available from Dow Chemical, Union Carbide or Dupont-Mitsui Polychemicals Co., Ltd., all of which make suitable polyethylenes. The particular polyethylene chosen can be selected for its density and melt flow viscosity. For example, materials with lower melt flow viscocity can be chosen to improve the melt flow of melted PTC material 50 into foam 60 as is described herein. Improved melt flow of material 50 into foam 60 in turn improves the thermal conductivity between the two material as is also described herein.

It is generally has been determined that the $T_S$ of a polymeric PTC composition is within the region of the glass transition temperature ($T_G$), which is well below the melt temperature ($T_M$) of the crystalline polymer. If the thermal expansion coefficient of the polymer is sufficiently high above the $T_G$, a highly non-linear PTC effect will occur. Preferably, base polymers 190 has a high degree of crystallinity but it can also be semi-crystalline. However, in order to fabricate a polymer composition with a highly nonlinear "square" PTC effect, it is preferable that the polymer has a $T_G$ in the temperature range of 70° C. to 300° C.; though, other range for $T_G$ may also be used.

The conductive particles 192 can be carbon particles. Other particle types include without limitation, silver, tin, nickel, gold, copper, platinum, palladium, magnesium, aluminum, molybdenum, tungsten, tantalum, zinc, cobalt or a combination thereof.

The conductive particles are mixed into a melt-state polymer until the particles are well dispersed. By any technique known in the art, the mixing is accomplished in a system that provides a temperature higher than the melting point of the polymeric base 190. In mixing the polymer base 190 with the particles 192, and optional additives described below, the objective of mixing is to create a uniform distribution of particles within the matrix. For example, the mixing temperature and time must be properly controlled so that the conductive particles will uniformly create conductive paths within the matrix as the PTC body operates. An excessive mixing time may cause a separation between conductive particles resulting in non-uniform conductive paths as the polymer component polymerizes from a liquid into a solid. Non-uniform formation of conductive paths is undesirable because it can result in internal arcing during its operation.

The thermoplastic polymer base 190 can carry other additives known in the art, such as flame retardants or anti-arcing compositions, an anti-oxidizing agent (magnesium oxide or titanium oxide), an anti-ozonizing agent, a cross-linking agent or any combination thereof. In the fabrication process, the mixture can also be treated with various processes (e.g., gamma, UV irradiation etc.) to cross-link the polymer or co-polymers of the matrix. However, it has been found that it is not necessary to cross-link the polymer base material 190 to provide a fully functional PTC composite.

The polymeric PTC composition thereafter can be pressed into sheet material for further processing. For example, foil electrodes can be attached on either side of the PTC sheet for making a thermistor. When used as a thermal sensor or constant temperature heater, the PTC composition can be molded or extruded in any suitable shape.

Many embodiments of the invention employ the use of graphite foams (described herein) for enhancing the performance of the PTC systems for tissue sealing. However, it will also be appreciated that various embodiments of the invention also contemplate other heat subtraction and heat sinks technologies known in the art which can be used in place of or in conjunction with graphite foam. It further can be seen that passive or active systems for heat diffusion will work best if distributed throughout the polymeric PTC material.

Thus the scope of the invention includes any passive heat sink coupled to the PTC composition, such as any thermally conductive heat exchange devices.

The scope of the invention also includes oriented thermally conductive fibers or filaments (e.g., carbon fibers) that are molded directly into the polymeric composition to diffuse heat, either uni-directionally, bi-directionally or omni-directionally.

The scope of the invention includes any active heat sinks in the form of cooling channels, heat pipes or thermosiphons and the like as known in the art of thermal management.

The scope of the invention also includes any active cooling systems of the types disclosed in a related electrosurgical instrument in co-pending U.S. patent application Ser. No. 10/781,925 filed Feb. 14, 2004 titled Electrosurgical Instrument and Method of Use.

4. Tissue interactions with related PTC devices having heat diffusivity component. A discussion will now be presented of methods of using embodiments PTC based electrosurgical instruments and devices including tissue interactions. Embodiments of the invention can be configured to utilize PTC materials to provide several thermal effects including ohmic heating of tissue, denaturation of proteins in tissue and the welding of tissue. In particular various embodiments can utilize ohmic heating to rapidly denature proteins in a target tissue volume. This denatured collagen can then be fused (e.g., by the application of force) rapidly form a new collagen matrix. Thus, in use, such ohmic heating allows for the creation of welds or seals in tissue that have high strength immediately post treatment because the formation of the new collagen matrix from the denatured proteins adds a high strength collagen component to the strength of the seal, in essence using the natural high strength material of collagen to form the seal. Such methods are particularly suitable for forming high strength welds in various blood vessels including arteries as well as thick tissues, tissue bundles and other collagen containing materials. In the case of arterial welds, embodiments of such method allows for the rapid creation of not only a high strength weld, but a high strength fluidic seal which will not leak from arterial pressure.

In other embodiments, the PTC based electrosurgical devices can be configured for using conductive heating as opposed to ohmic heating as means to weld or seal tissue. While high strength welds are desirable in a number of surgical applications, there remain other situations in microsurgeries, neurosurgeries, sealing fragile veins, sealing thin membranes and the like wherein high strength welds are not critical. In some of these sealing applications, the use of conductive heating (contrasted with ohmic heating) may be desirable. For example, in neurosurgery it is often necessary to seal very small vessels that carry limited pressures. Here the principal objectives are prevention of sticking and collateral thermal or other damage.

Figure 10:
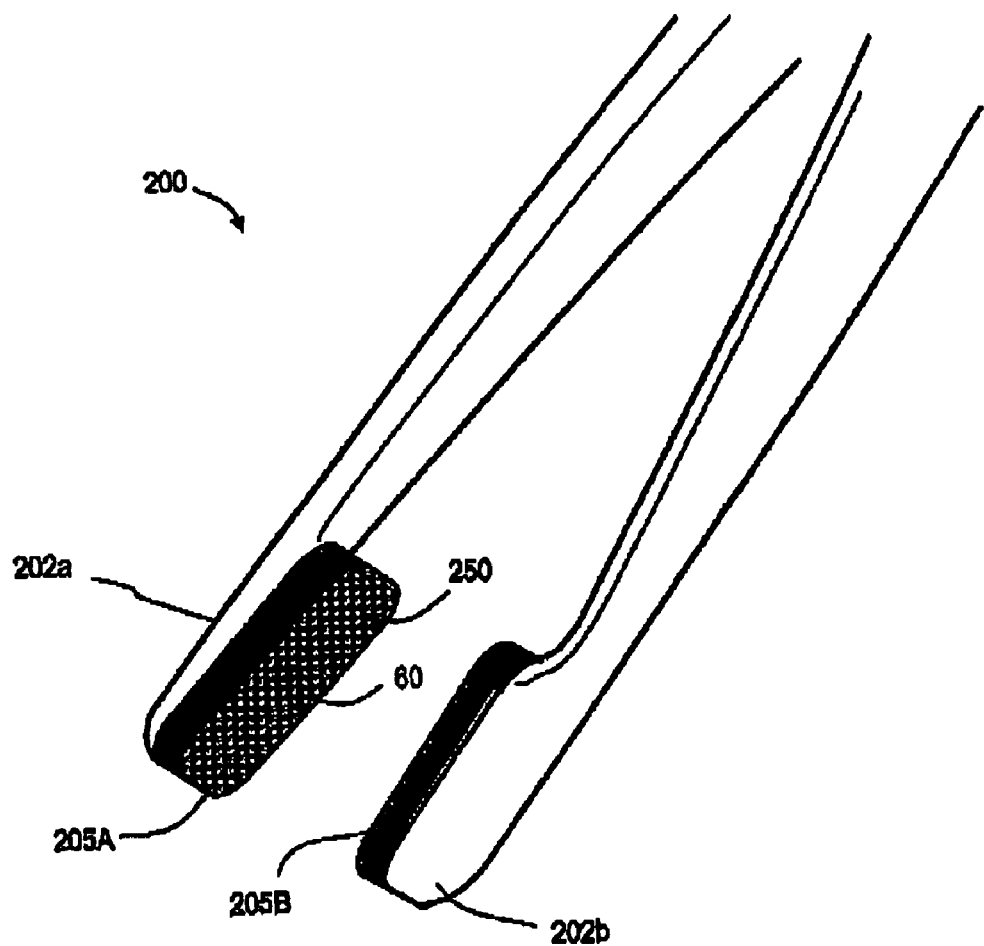
FIG. 10 is a view of forceps used in neurosurgery that has novel PTC energy-delivery surfaces.

FIG. 10 illustrates an embodiment of a forceps 200 configured for use in neurosurgery and related applications. The forceps 200 include tines or jaw elements 202*a* and 202*b*. In the embodiment of FIG. 10, one or both engagement surfaces 205A and 205B can comprise in part a polymeric PTC composition 250 that is capable of I²R (Joule) internal heating—which is unlike all previous embodiments. Again, the PTC composition 250 is carried in the voids of a graphite cellular material 60, such as POCO-FOAM™. The graphite foam can extend to the tissue-engaging surface. In operation, it can be understood that the PTC composition can be selected to provide a selected temperature for sealing a very thin tissue. The graphite foam will then function to provide very uniform temperature across the engagement surfaces, which will insure that the thin tissues are heated uniformly and prevent hot spots, which can result in sticking.

Figure 11:
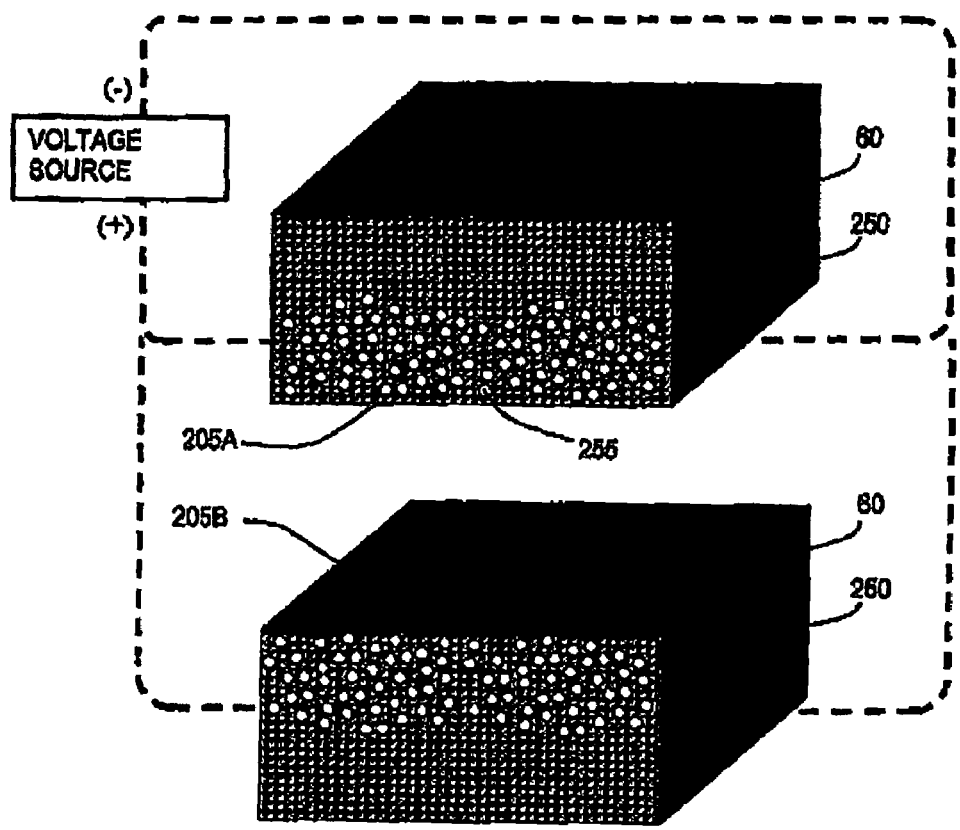
FIG. 11 is an enlarged view of an alternative PTC surfaces similar to that of FIG. 10.

In a closely related embodiment illustrated in FIG. 11, the PTC composition 250 can carry microencapsulated phase change materials (PCMs) 255 as disclosed in detail in U.S. Provisional Patent Application Ser. No. 60/558,672 filed Apr. 1, 2004 titled Surgical Sealing Surfaces and Methods of Use. In that disclosure, the invention provided an energy modulating surface for interfacing with tissue. The tissue-engaging surface can be in a surgical probe or jaw structure. The energy modulating surface uses PCMs to protect the engaged tissue from excessively high local temperatures that result in char and sticking through the physical phenomenon of the absorption of the PCMs latent heat of fusion. The phase change material is capable of practically instantaneous localized absorption of the material's latent heat to stabilize tissue temperature at the probe-tissue interface. The temperature modulation can occur in a localized manner, or "pixelated" manner, across the surface of the energy modulating material. The energy modulating surface can increase the strength of tissue welds, in addition to preventing charring and sticking.

Figure 12:
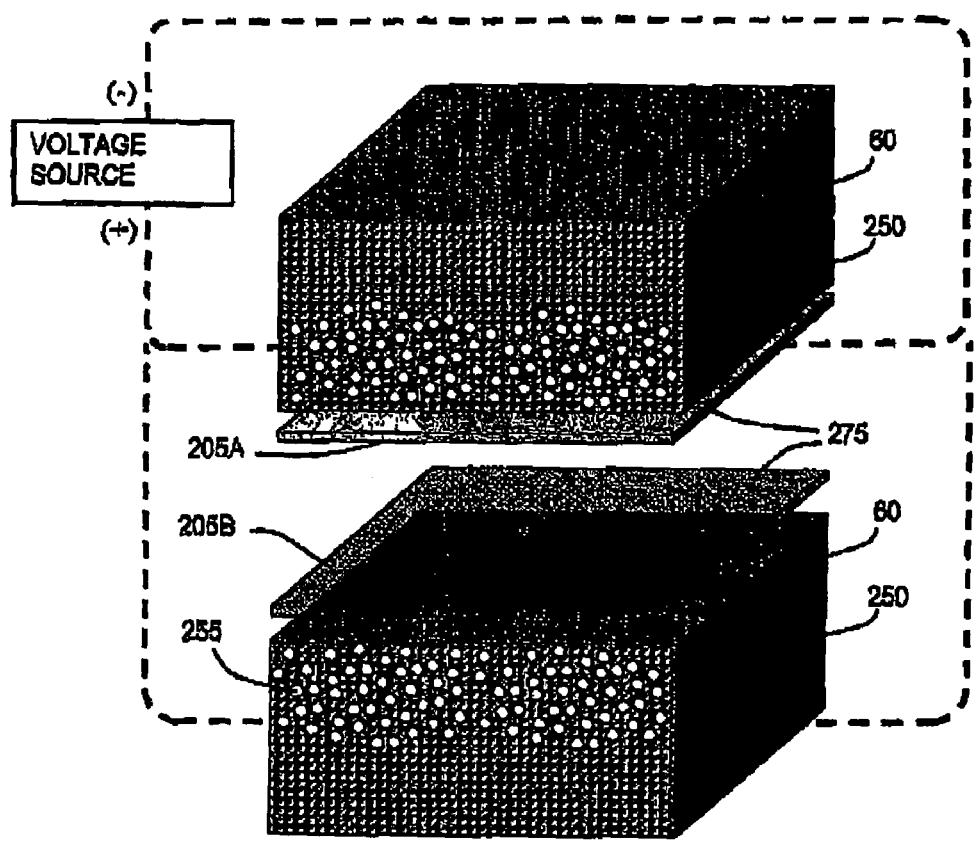
FIG. 12 is an enlarged view of an alternative PTC surfaces similar to that of FIG. 11.

In FIG. 12, a final embodiment for prevention of tissue sticking is shown which is the same as described in FIG. 11 with the addition of thin surface layer 275 (exploded view) of a non-conductive polymer such as a silicone or the like. This polymer layer can be configured to allow substantially all electrosurgical and/or thermal energy to be conducted therethrough, but will prevent electrical arcs at the interface of the tissue and the electrosurgical surface as well as limiting tissue adherence and sticking to the surface. It should be appreciated that a similar thin polymer layer 275 can be added to any of the surfaces of FIGS. 3-9 wherein the polymer layer will not substantially hinder current flow to cause ohmic heating in the engaged tissue. Such non-conductive polymer surface layers can include a thin film material that is bonded to the electrosurgical surface or a flowable material that is polymerized and bonded in place after application to the electrosurgical surface.

Embodiments of the invention further include any thermal energy delivery surface for use in surgical sealing that carries a PCM material in a polymer sealing surface. Embodiments of the invention also encompasses any thermal energy delivery surface that carries oriented conductive graphite or similar elements for optimizing performance by its thermal diffusivity.

It should be appreciated that the system and electrode arrangement of FIG. 6 can be utilized to provide thermal sensing and $I^2R$ heating of any conductive subject material, such as metals, polymeric compositions, ceramic compositions, combinations thereof and the like.

Conclusion: The foregoing description of various embodiments of the invention has been presented for purposes of illustration and description. It is not intended to limit the invention to the precise forms disclosed. Many modifications, variations and refinements will be apparent to practitioners skilled in the art. Further, the teachings of the invention have broad application in the electrosurgical and laparoscopic device fields as well as other fields which will be recognized by practitioners skilled in the art. Such fields can include without limitation various minimally invasive and endoscopic methods including those in the areas of urological, gynecological, ENT, GI, dermatological, plastic surgery, oncological, orthopedic, dental and other medical fields known in the art.

Elements, characteristics, or acts from one embodiment can be readily recombined or substituted with one or more elements, characteristics or acts from other embodiments to form numerous additional embodiments within the scope of the invention. Hence, the scope of the present invention is not limited to the specifics of the exemplary embodiment, but is instead limited solely by the appended claims.

What is claimed is:

1. A matrix for an electrosurgical energy delivery surface, the matrix comprising:
   a positive temperature coefficient of resistance (PTCR) material, the material having a substantially conductive state and a substantially non-conductive state; and
   a heat exchange material disposed within an interior of the matrix, the heat exchange material having a structure configured to provide directional thermal diffusivity for exchanging heat with the PTCR material to cause rapid switching of the PTCR material between the conductive state and the non-conductive state.

2. The matrix of claim 1, wherein the heat exchange material conducts heat from the PTCR material to cause rapid switching of the PTCR material between the conductive state and the non-conductive state.

3. The matrix of claim 1, wherein the heat exchange material has a uni-directional thermal diffusivity.

4. The matrix of claim 1, wherein the structure is a cellular structure, a non-amorphous structure or a crystalline structure.

5. The matrix of claim 1, wherein the matrix is carried in a tissue-contacting surface of an electrosurgical device.

6. The matrix of claim 1, wherein the matrix is carried in at least one jaw of an electrosurgical device.

7. The matrix of claim 1, wherein the PTCR material is electrically insulated from the heat exchange material.

8. The matrix of claim 1, wherein the heat exchange material comprises at least one graphite element.

9. The matrix of claim 1, wherein at least a portion of the matrix comprises a graphite foam structure.

10. The matrix of claim 9, wherein at least a portion of the graphite foam structure is a cellular structure, an open cell structure, a non-amorphous structure or a crystalline structure.

11. The matrix of claim 9, wherein the graphite foam structure comprises a plurality of thermally conductive filaments.

12. The matrix of claim 11, wherein at least a portion of the thermally conductive filaments are oriented to conduct heat in a unidirectional, bi-directional, or omni-directional manner.

13. The matrix of claim 1, wherein the heat exchange material is coupled to a heat sink.

14. The matrix of claim 1, wherein the heat exchange material comprises a phase change material.

15. The matrix of claim 1, wherein the heat exchange material is a thermosiphon.

16. The matrix of claim 1, wherein the heat exchange material has an electrically non-conductive polymer surface layer.

* * * * *

UNITED STATES PATENT AND TRADEMARK OFFICE
CERTIFICATE OF CORRECTION

PATENT NO.          : 7,220,951 B2                                  Page 1 of 14
APPLICATION NO.  : 11/110363
DATED                    : May 22, 2007
INVENTOR(S)         : Csaba Truckai et al.

It is certified that error appears in the above-identified patent and that said Letters Patent is hereby corrected as shown below:

Please replace FIG. 1A (Prior Art) on Sheet 1 of 14 with the following replacement Figure:

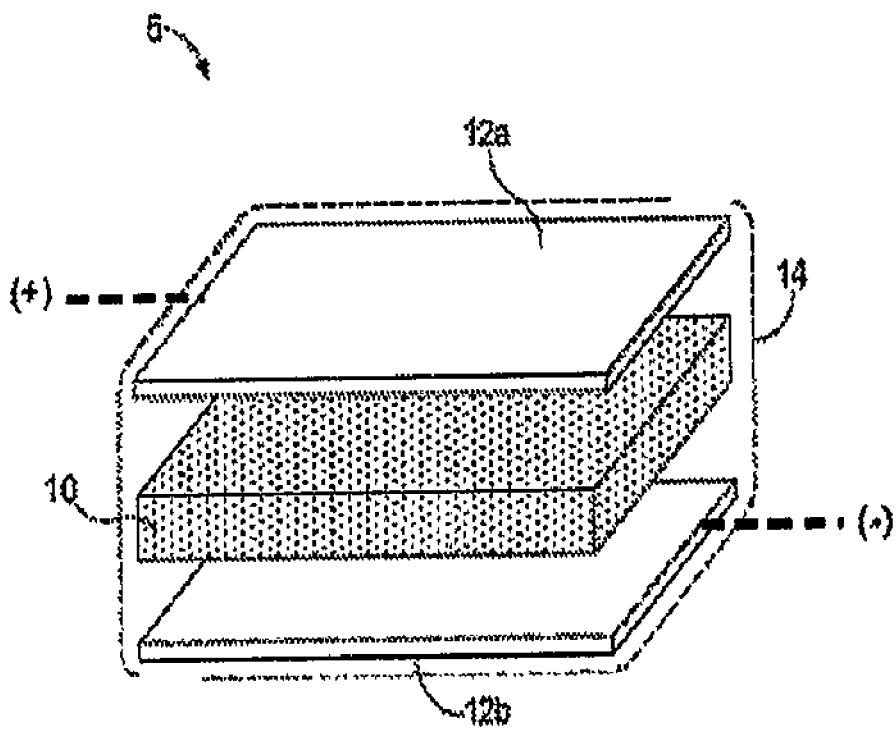

FIG. 1A
(PRIOR ART)

UNITED STATES PATENT AND TRADEMARK OFFICE
CERTIFICATE OF CORRECTION

PATENT NO. : 7,220,951 B2
APPLICATION NO. : 11/110363
DATED : May 22, 2007
INVENTOR(S) : Csaba Truckai et al.

It is certified that error appears in the above-identified patent and that said Letters Patent is hereby corrected as shown below:

Please replace FIG. 1B (Prior Art) on Sheet 2 of 14 with the following replacement Figure:

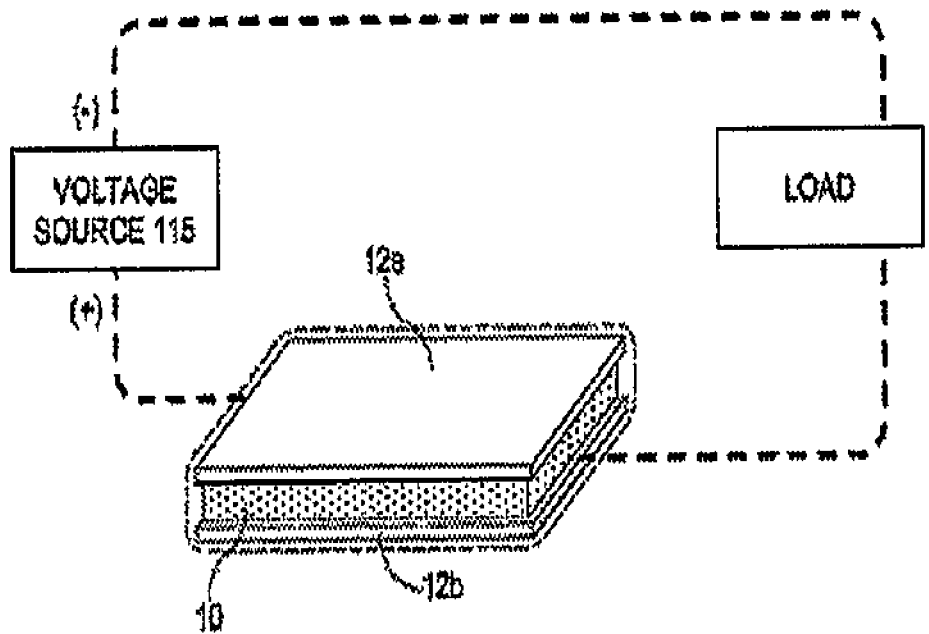

FIG. 1B
(PRIOR ART)

UNITED STATES PATENT AND TRADEMARK OFFICE
CERTIFICATE OF CORRECTION

PATENT NO.         : 7,220,951 B2                                        Page 3 of 14
APPLICATION NO.    : 11/110363
DATED              : May 22, 2007
INVENTOR(S)        : Csaba Truckai et al.

It is certified that error appears in the above-identified patent and that said Letters Patent is hereby corrected as shown below:

Please replace FIG. 1C (Prior Art) on Sheet 3 of 14 with the folowing replacement Figure:

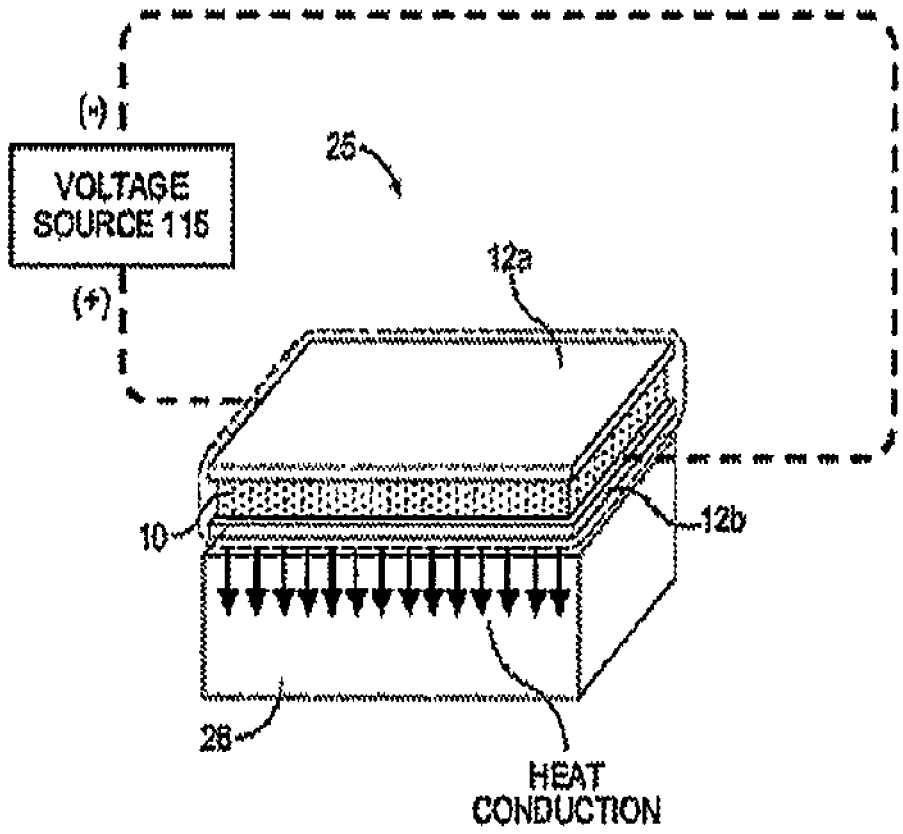

UNITED STATES PATENT AND TRADEMARK OFFICE
CERTIFICATE OF CORRECTION

| | | |
|---|---|---|
| PATENT NO. | : 7,220,951 B2 | Page 4 of 14 |
| APPLICATION NO. | : 11/110363 | |
| DATED | : May 22, 2007 | |
| INVENTOR(S) | : Csaba Truckai et al. | |

It is certified that error appears in the above-identified patent and that said Letters Patent is hereby corrected as shown below:

Please replace FIG. 2 on Sheet 4 of 14 with the following replacement Figure:

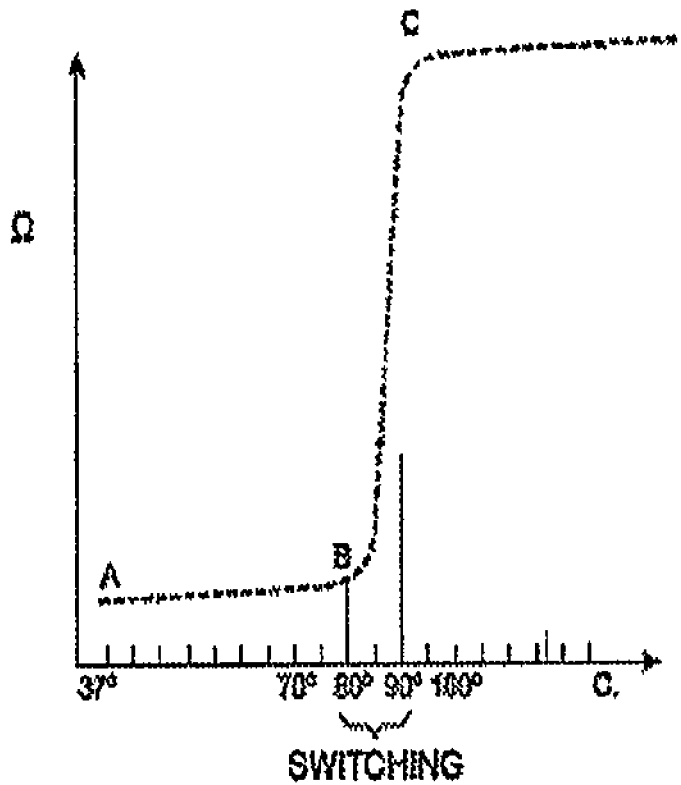

FIG. 2

UNITED STATES PATENT AND TRADEMARK OFFICE
CERTIFICATE OF CORRECTION

PATENT NO.        : 7,220,951 B2                                           Page 5 of 14
APPLICATION NO.   : 11/110363
DATED             : May 22, 2007
INVENTOR(S)       : Csaba Truckai et al.

It is certified that error appears in the above-identified patent and that said Letters Patent is hereby corrected as shown below:

Please replace FIG. 3 on Sheet 5 of 14 with the following replacement Figure:

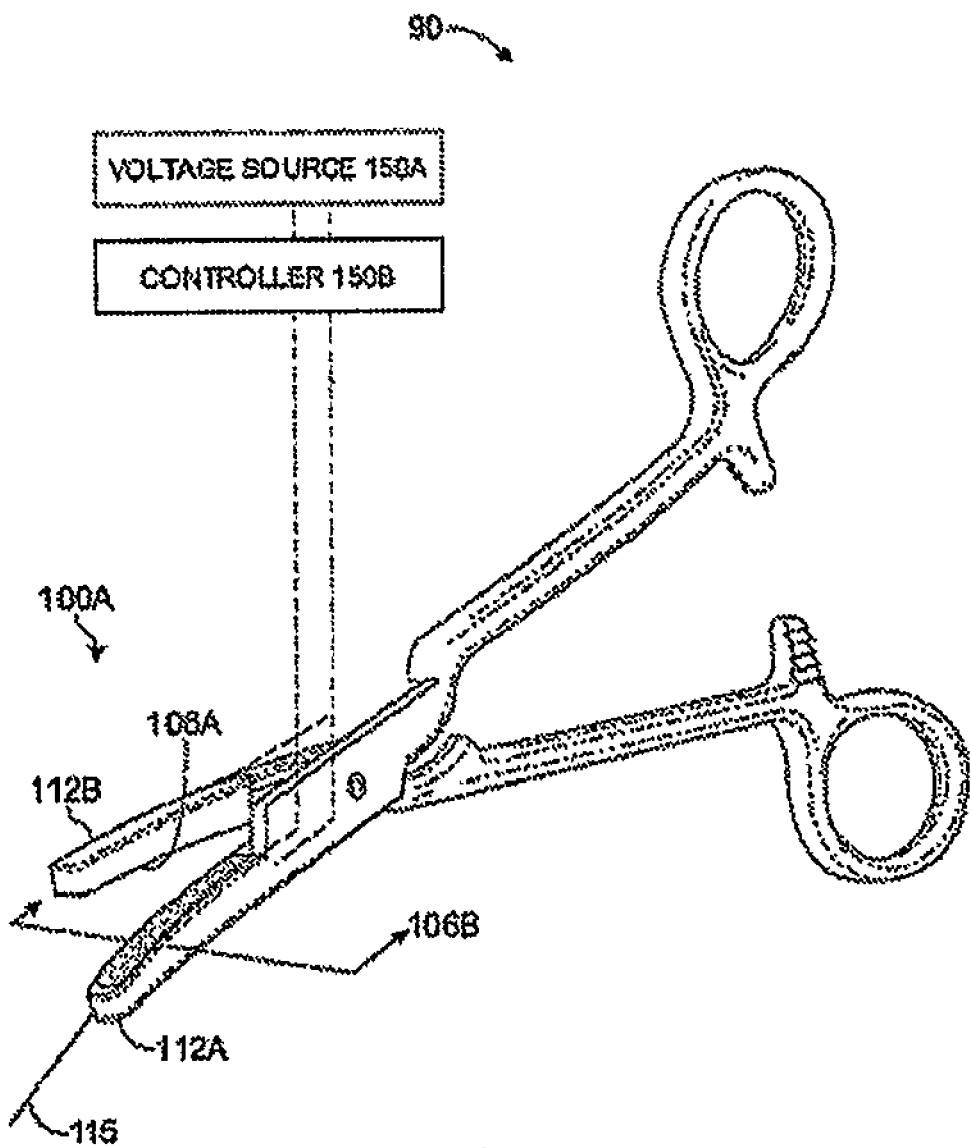

FIG. 3

UNITED STATES PATENT AND TRADEMARK OFFICE
CERTIFICATE OF CORRECTION

PATENT NO. : 7,220,951 B2  Page 6 of 14
APPLICATION NO. : 11/110363
DATED : May 22, 2007
INVENTOR(S) : Csaba Truckai et al.

It is certified that error appears in the above-identified patent and that said Letters Patent is hereby corrected as shown below:

Please replace FIG. 4 on Sheet 6 of 14 with the following replacement Figure:

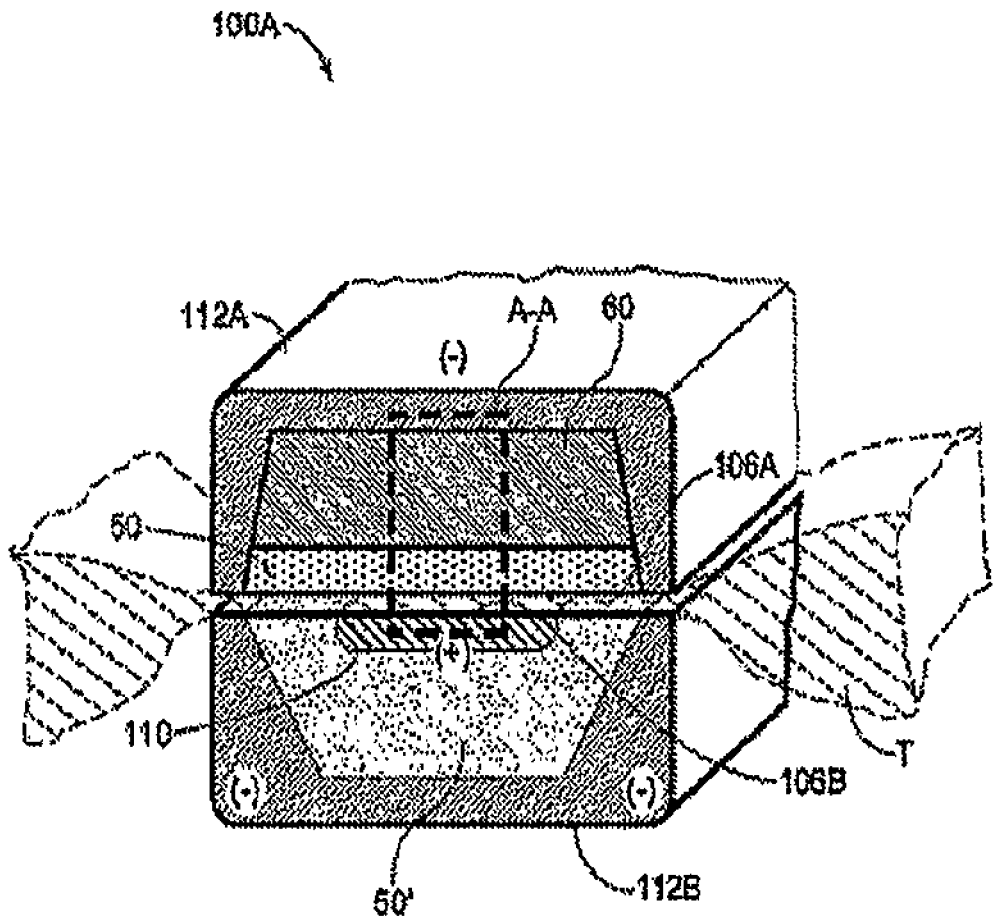

FIG. 4

UNITED STATES PATENT AND TRADEMARK OFFICE
CERTIFICATE OF CORRECTION

PATENT NO.       : 7,220,951 B2                                Page 7 of 14
APPLICATION NO.  : 11/110363
DATED            : May 22, 2007
INVENTOR(S)      : Csaba Truckai et al.

It is certified that error appears in the above-identified patent and that said Letters Patent is hereby corrected as shown below:

Please replace FIG. 5 on Sheet 7 of 14 with the following replacement Figure:

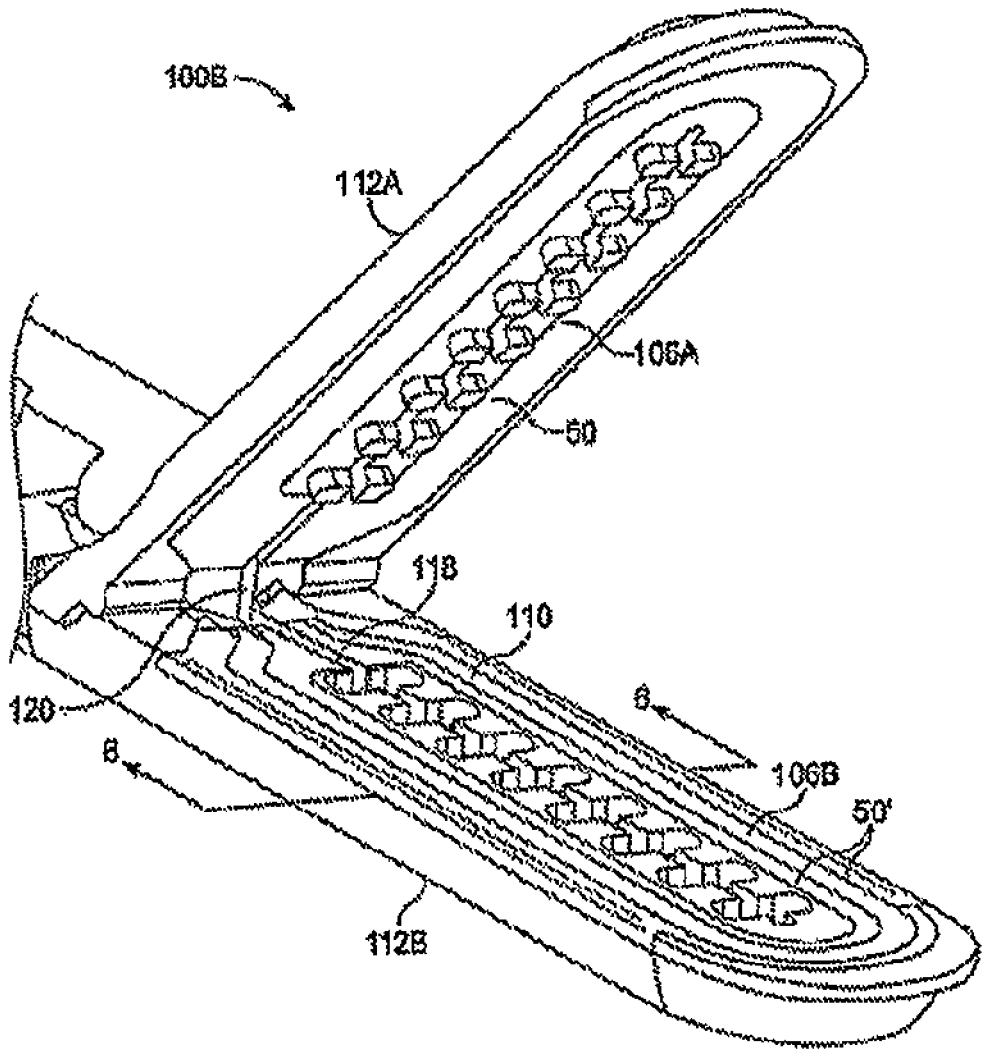

FIG. 5

UNITED STATES PATENT AND TRADEMARK OFFICE
CERTIFICATE OF CORRECTION

PATENT NO. : 7,220,951 B2 Page 8 of 14
APPLICATION NO. : 11/110363
DATED : May 22, 2007
INVENTOR(S) : Csaba Truckai et al.

It is certified that error appears in the above-identified patent and that said Letters Patent is hereby corrected as shown below:

Please replace FIG. 6 on Sheet 8 of 14 with the following replacement Figure:

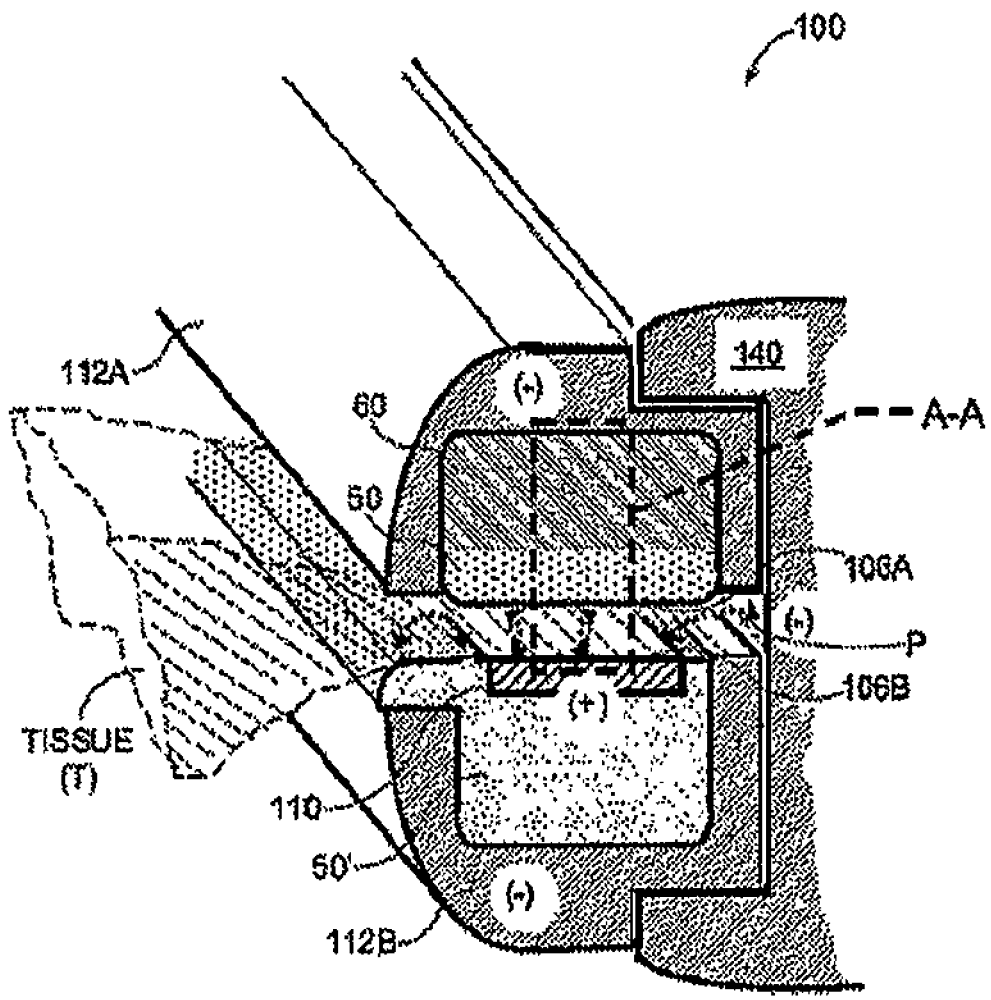

FIG. 6

UNITED STATES PATENT AND TRADEMARK OFFICE
CERTIFICATE OF CORRECTION

PATENT NO.        : 7,220,951 B2
APPLICATION NO.   : 11/110363
DATED             : May 22, 2007
INVENTOR(S)       : Csaba Truckai et al.

It is certified that error appears in the above-identified patent and that said Letters Patent is hereby corrected as shown below:

Please replace FIG. 7 on Sheet 9 of 14 with the following replacement Figure:

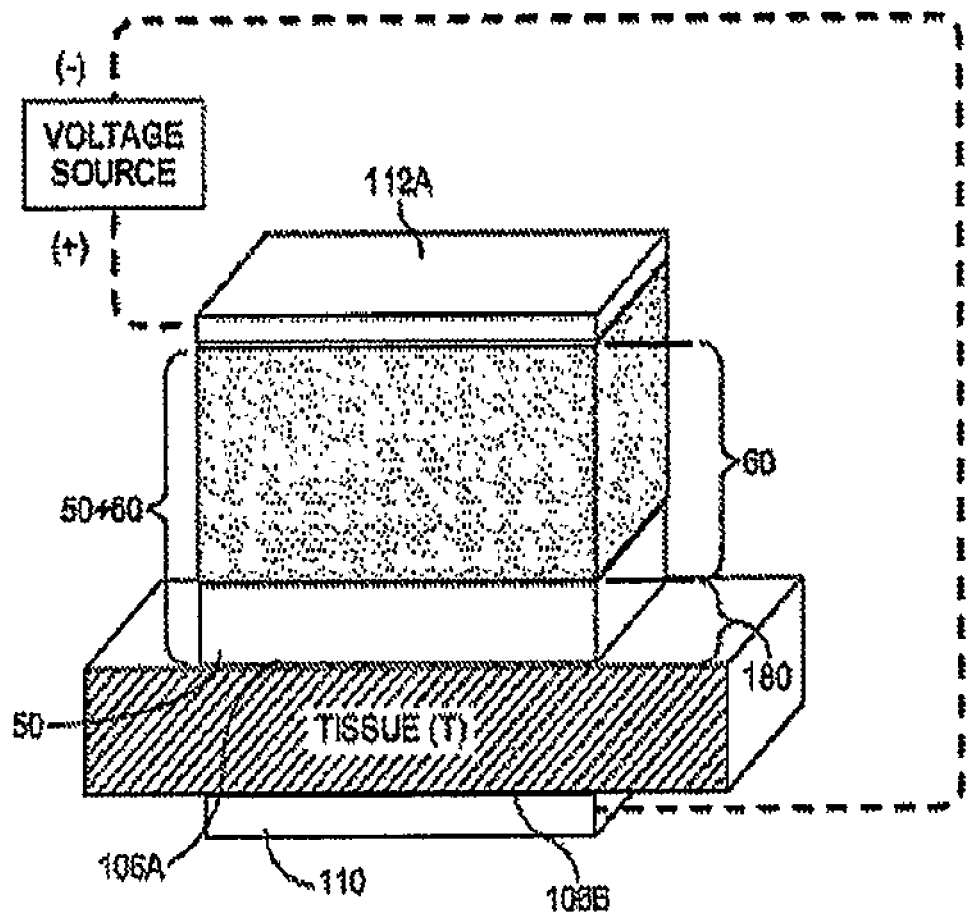

FIG. 7

UNITED STATES PATENT AND TRADEMARK OFFICE
CERTIFICATE OF CORRECTION

PATENT NO.       : 7,220,951 B2
APPLICATION NO.  : 11/110363
DATED            : May 22, 2007
INVENTOR(S)      : Csaba Truckai et al.

It is certified that error appears in the above-identified patent and that said Letters Patent is hereby corrected as shown below:

Please replace FIG. 8 on Sheet 10 of 14 with the following replacement Figure:

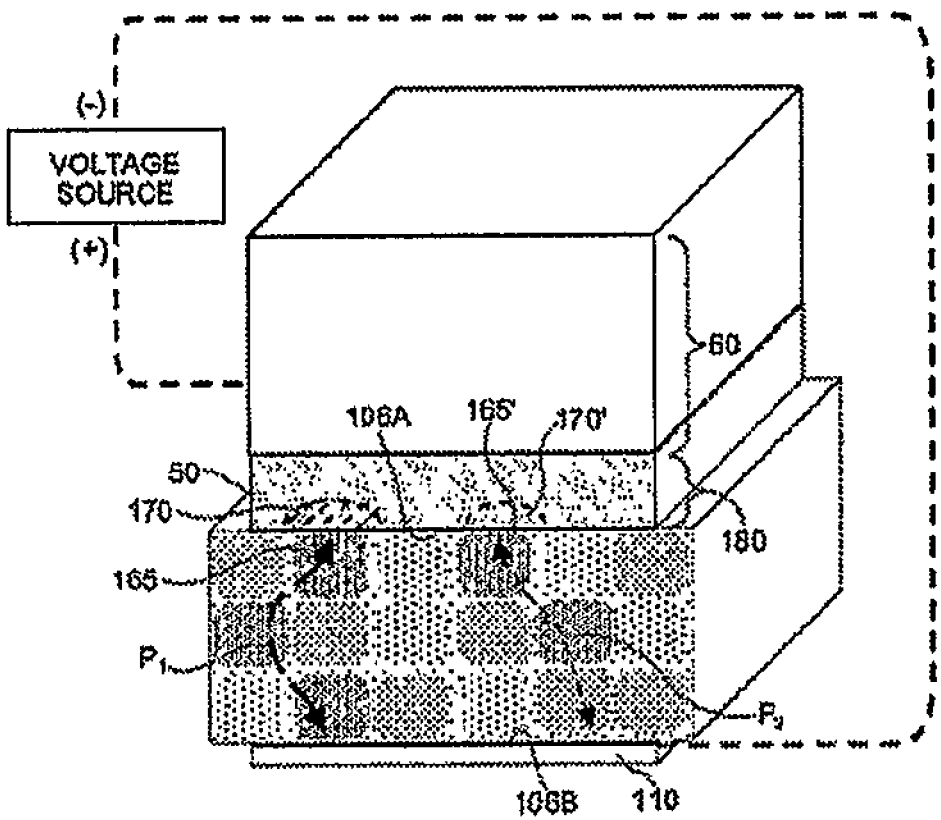

FIG. 8

UNITED STATES PATENT AND TRADEMARK OFFICE
CERTIFICATE OF CORRECTION

PATENT NO.      : 7,220,951 B2
APPLICATION NO. : 11/110363
DATED           : May 22, 2007
INVENTOR(S)     : Csaba Truckai et al.

It is certified that error appears in the above-identified patent and that said Letters Patent is hereby corrected as shown below:

Please replace FIG. 9 on Sheet 11 of 14 with the following replacement Figure:

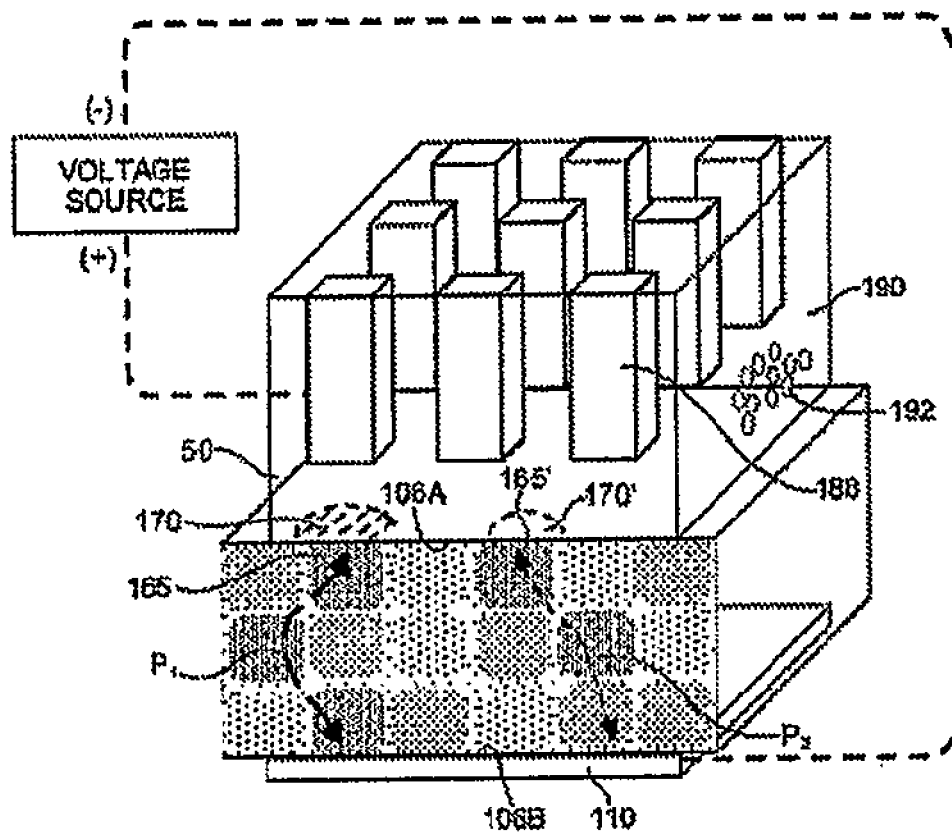

FIG. 9

UNITED STATES PATENT AND TRADEMARK OFFICE
CERTIFICATE OF CORRECTION

PATENT NO. : 7,220,951 B2
APPLICATION NO. : 11/110363
DATED : May 22, 2007
INVENTOR(S) : Csaba Truckai et al.

It is certified that error appears in the above-identified patent and that said Letters Patent is hereby corrected as shown below:

Please replace FIG. 10 on Sheet 12 of 14 with the following replacement Figure:

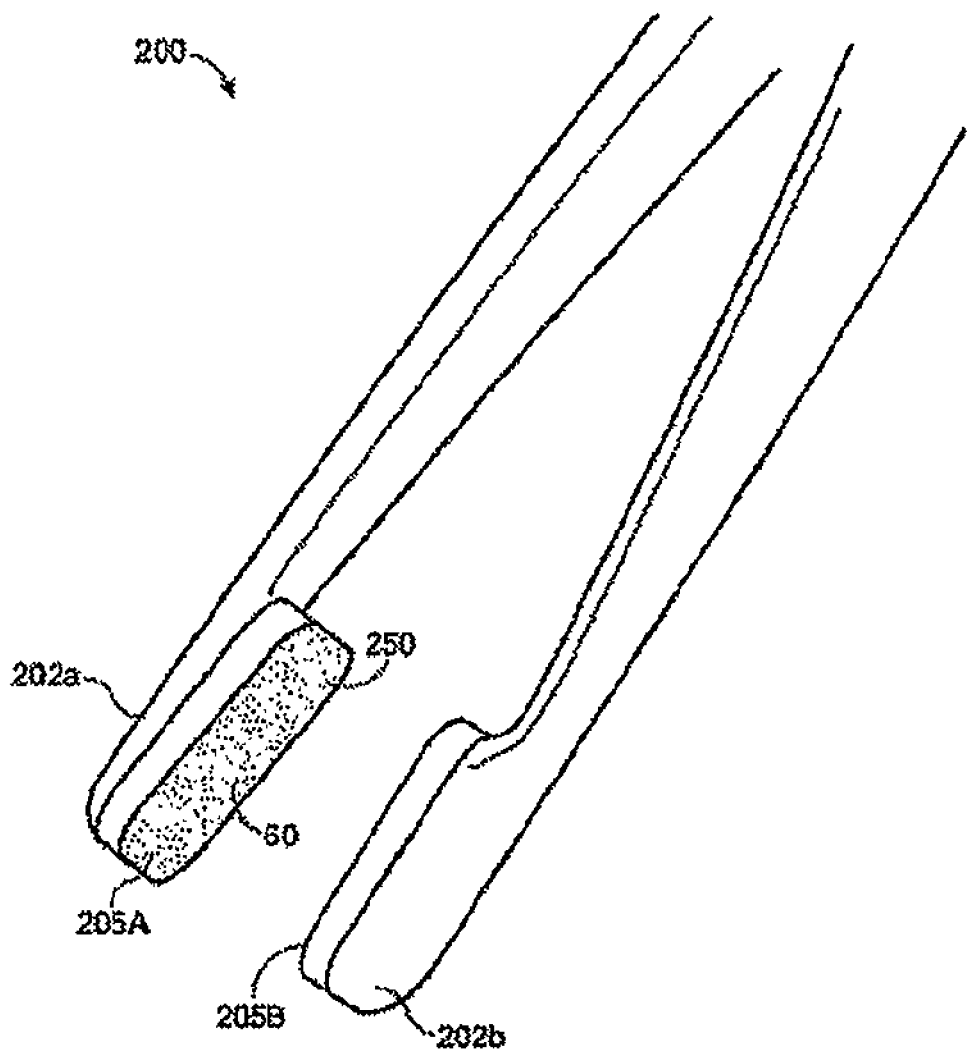

FIG. 10

UNITED STATES PATENT AND TRADEMARK OFFICE
CERTIFICATE OF CORRECTION

| | |
|---|---|
| PATENT NO. | : 7,220,951 B2 |
| APPLICATION NO. | : 11/110363 |
| DATED | : May 22, 2007 |
| INVENTOR(S) | : Csaba Truckai et al. |

It is certified that error appears in the above-identified patent and that said Letters Patent is hereby corrected as shown below:

Please replace FIG. 11 on Sheet 13 of 14 with the following replacement Figure:

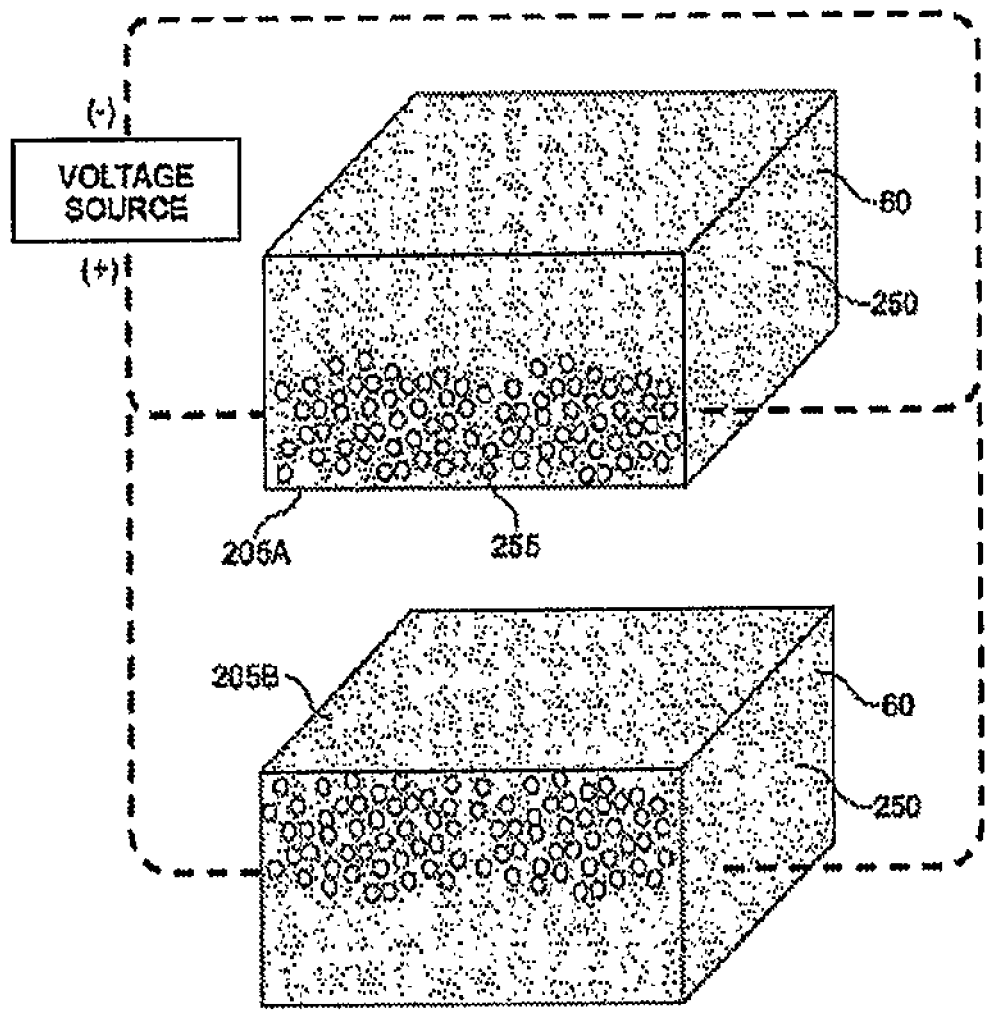

FIG. 11

```
ERROR: interrupt
OFFENDING COMMAND: xfile

STACK:

0
-mark-
1
false
false
1457
1108
1
4
2
8
1
2
```